United States Patent
Gotoh

(10) Patent No.: US 7,620,141 B2
(45) Date of Patent: Nov. 17, 2009

(54) X-RAY IMAGING APPARATUS

(75) Inventor: Keiichi Gotoh, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 0 days.

(21) Appl. No.: 12/161,949

(22) PCT Filed: Jan. 23, 2007

(86) PCT No.: PCT/JP2007/050975
§ 371 (c)(1),
(2), (4) Date: Jul. 23, 2008

(87) PCT Pub. No.: WO2007/086369
PCT Pub. Date: Aug. 2, 2007

(65) Prior Publication Data
US 2009/0010380 A1    Jan. 8, 2009

(30) Foreign Application Priority Data
Jan. 24, 2006    (JP) .............................. 2006-015063

(51) Int. Cl.
H05G 1/60    (2006.01)
H05G 1/64    (2006.01)
(52) U.S. Cl. .................... 378/5; 378/19; 378/98.12
(58) Field of Classification Search .................. 378/5, 378/8, 9, 19, 62, 98.8–98.12
See application file for complete search history.

(56) References Cited

U.S. PATENT DOCUMENTS

| | | | |
|---|---|---|---|
| 6,421,419 B1 * | 7/2002 | Sakaida | 378/98.11 |
| 6,754,398 B1 * | 6/2004 | Yamada | 382/260 |
| 2004/0022359 A1 | 2/2004 | Acharya et al. | |
| 2004/0101089 A1 | 5/2004 | Karau et al. | |
| 2004/0102688 A1 | 5/2004 | Walker et al. | |

FOREIGN PATENT DOCUMENTS

| | | |
|---|---|---|
| JP | 06-022219 A | 1/1994 |
| JP | 11-188024 A | 7/1999 |
| JP | 2004-065975 A | 3/2004 |
| JP | 2004-174260 A | 6/2004 |
| JP | 2004-188187 A | 7/2004 |
| JP | 2005-058309 A | 3/2005 |
| JP | 2007-021184 A | 2/2007 |

OTHER PUBLICATIONS

International Search Report for the Application No. PCT/JP2007/050975 mailed May 1, 2007.

* cited by examiner

Primary Examiner—Irakli Kiknadze
(74) Attorney, Agent, or Firm—Cheng Law Group, PLLC

(57) ABSTRACT

The present invention relates to an X-ray imaging apparatus using a technique for preventing artifacts appearing in 3D X-ray images. The technique involves subtraction images obtained by an energy subtraction unit serving as the basis for a 3D reconstruction process for acquiring a 3D X-ray image selectively showing a site of interest in a patient. The technique also involves an image subtraction process carried out by the energy subtraction unit according to weights set by a weight setter which selects only the site of interest in the patient, and eliminates soft tissue forming a background around the site of interest. As a result, even if body motion occurs with the soft tissue forming the background around the site of interest of the patient while subtraction images are acquired one after another by the energy subtraction unit, the body motion in the soft tissue of the patient never appears as artifacts on the subtraction images, or on a 3D X-ray image acquired on the basis of the subtraction images.

8 Claims, 17 Drawing Sheets output voltages of high-voltage generator output periods of X-ray detection signals

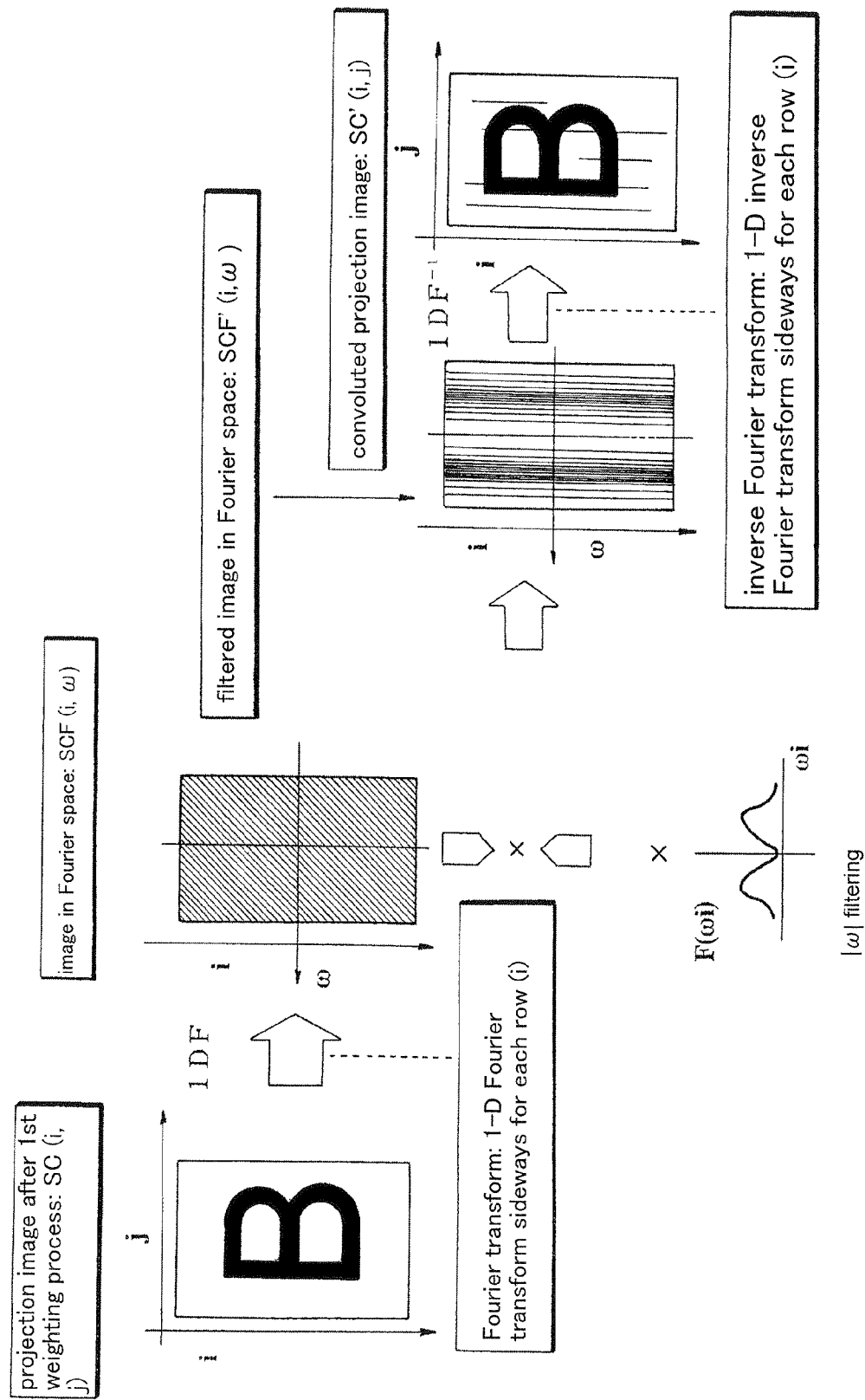

X-RAY IMAGING APPARATUS

TECHNICAL FIELD

This invention relates to an X-ray imaging apparatus for obtaining 3D X-ray images selectively showing a site of interest in an object under examination. More particularly, the invention relates to a technique for preventing artifacts appearing in 3D X-ray images.

BACKGROUND ART

In recent years, X-ray imaging apparatus often use a subtraction technique which carries out an image subtraction process on two X-ray images of the same site picked up with different photographing conditions, thereby to obtain a new subtraction image.

A specific difference factor of photographing conditions between the two X-ray images may be energy intensity of X-ray beams irradiating the object under examination. In the case of a subtraction technique of the dual energy mode using two types of X-ray beams, i.e. with high energy and low energy, a high-energy X-ray image is obtained from the X-ray beam of high energy, and a low-energy X-ray image from the X-ray beam of low energy, and thereafter a subtraction image is obtained by carrying out a subtraction between the high-energy X-ray image and low-energy X-ray image based on predetermined weights applied to the high- and low-energy X-ray images. Further, by suitably adjusting the level of weighting set beforehand to the X-ray images, it is possible to obtain, as a subtraction image, a bone image from which soft tissue is eliminated, or, conversely, a soft tissue image from which bones are eliminated (see Patent Document 1).

A specific difference factor of photographing conditions between the two X-ray images may be whether or not a contrast medium is injected into the object under examination. In the case of a subtraction technique of the contrast medium injection mode accompanied by injection of a contrast medium into the object under examination, X-ray images are obtained before injection of the contrast medium, and X-ray images after injection of the contrast medium, and thereafter subtraction is carried out to obtain subtraction images selecting a site into which the contrast medium has been injected. In the case of angiography in which a contrast medium is injected into blood vessels, an X-ray imaging apparatus carries out a subtraction after obtaining X-ray images before injecting the contrast medium into the blood vessels, and X-ray images after injecting the contrast medium into the blood vessels, to obtain subtraction images selecting, as the site of interest, the blood vessels into which the contrast medium has been injected.

In addition, a conventional X-ray imaging apparatus using the subtraction technique of the contrast medium injection mode carries out a 3D reconstruction for obtaining a 3D image showing blood vessels which are a contrast medium injection site, based on a plurality of subtraction images of the same photographic site picked up from different photographing directions. Specifically, before injecting the contrast medium into the blood vessels, X-ray images in different revolutional phases are successively obtained while revolving an X-ray tube for X-ray emission and a two-dimensional X-ray detector for transmitted X-ray image detection around the patient. Next, after injecting the contrast medium into the blood vessels, as before the contrast medium injection, X-ray images in different revolutional phases are successively obtained while revolving the X-ray tube for X-ray emission and the two-dimensional X-ray detector for transmitted X-ray image detection around the patient.

Then, a subtraction image is obtained for each revolutional phase by carrying out an image subtraction process for two X-ray images picked up before and after contrast medium injection, in the same revolutional phase of the X-ray tube and two-dimensional X-ray detector. Further, a 3D reconstruction process is carried out based on pixel signals of a large number of subtraction images obtained, and revolutional phases corresponding to geometric positions of the respective subtraction images, thereby obtaining a 3D X-ray image selectively showing the blood vessels in the patient as a site of interest. The 3D X-ray image of the blood vessels obtained in this way is used for checking the state of flow through the blood vessels or determination of a treatment policy.

[Patent Document 1]

Unexamined Patent Publication H11-188024 (Page 6, Col. 7 and FIG. 1)

DISCLOSURE OF THE INVENTION

Problem to be Solved by the Invention

However, the conventional X-ray imaging apparatus noted above has a problem that artifacts due to body motion of the patient frequently appear in a 3D X-ray image selectively showing blood vessels as a site of interest of the patient.

There occurs a considerable time difference between the two X-ray images picked up before and after the contrast medium injection to be subjected to the image subtraction process. A body motion tends to take place in the soft tissue of the patient from the time of obtaining the X-ray images before the contrast medium injection until the time of obtaining the X-ray images after the contrast medium injection. The body motion taking place in the soft tissue of the patient appears as artifacts in the 3D X-ray image, which become obstructive to checking of the state of flow through the blood vessels or determination of a treatment policy.

This invention has been made having regard to the state of the art noted above and its object is to provide an X-ray imaging apparatus capable of preventing artifacts due to body motion of an object under examination from appearing in a 3D X-ray image selectively showing a site of interest of the object under examination.

Means for Solving the Problem

To fulfill the above object, the invention in the first embodiment provides the following construction.

An X-ray imaging apparatus according to the invention defined in the first embodiment is characterized by comprising (A) an X-ray beam emitting device for emitting X-ray beams to an object under examination to be radiographed; (B) a two-dimensional X-ray detecting device for detecting transmitted X-ray images of the object under examination produced by emission of the X-ray beams to the object under examination, and outputting X-ray detection signals in real time; (C) a revolution device for revolving about the object under examination the X-ray beam emitting device and the two-dimensional X-ray detecting device opposed to each other across the object under examination; (D) an X-ray energy switching control device for performing X-ray energy switching control to switch the X-ray beams emitted from the X-ray beam emitting device alternately to high energy X-ray beams of high energy and to low energy X-ray beams of low energy; (E) a high energy image acquiring device for acquiring high energy X-ray photo images based on X-ray detection signals outputted from the two-dimensional X-ray detecting device as a result of emission of the high energy X-ray beams; (F) a low energy image acquiring device for acquiring low energy X-ray photo images based on X-ray detection signals outputted from the two-dimensional X-ray detecting device as a result of emission of the low energy X-ray beams; (G) a weight setting device for setting weights suitable for selecting a site of interest in the object under examination with respect to the high energy X-ray photo images and the low energy X-ray photo images; (H) an energy difference using subtraction device for acquiring subtraction images through an image subtraction process carried out, according to the weights set by the weight setting device, on high energy X-ray photo images and low energy X-ray photo images acquired adjacent each other in time; and (I) a 3D reconstruction device for carrying out a 3D reconstruction process, based on a plurality of subtraction images acquired by the energy subtraction device, to acquire a 3D X-ray image selectively showing the site of interest in the object under examination.

[Functions and Effects] When a 3D X-ray image is radiographed with the X-ray imaging apparatus according to the invention in the first embodiment, while the X-ray beam emitting device and the two-dimensional X-ray detecting device opposed to each other with the object under examination in between are revolved about the object under examination by the revolution device, the X-ray beam emitting device, under the X-ray energy switching control from the X-ray energy switching control device, repeatedly irradiates the object with a high energy X-ray beam having high energy and a low energy X-ray beam having low energy in alternation. In parallel with this, the two-dimensional X-ray detecting device detects a transmitted X-ray image of the object produced whenever the high energy X-ray beam or the low energy X-ray beam having low energy is emitted to the object, and outputs X-ray detection signals in real time.

Meanwhile, downstream of the two-dimensional X-ray detecting device, the high energy image acquiring device successively acquires high energy X-ray photo images based on X-ray detection signals outputted from the two-dimensional X-ray detecting device as a result of emission of the high energy X-ray beams, and the low energy image acquiring device successively acquires low energy X-ray photo images based on X-ray detection signals outputted from the two-dimensional X-ray detecting device as a result of emission of the low energy X-ray beams.

On the other hand, the energy difference using subtraction device successively acquires subtraction images through an image subtraction process carried out on the high energy X-ray photo images and low energy X-ray photo images acquired adjacent each other in time, according to appropriate weights set by the weight setting device to the high energy X-ray photo images and low energy X-ray photo images for selecting a site of interest in the object under examination. The high energy X-ray photo images and low energy X-ray photo images acquired as adjacent each other in time are photographed at substantially the same time. Since the high energy X-ray photo images and low energy X-ray photo images are different only in X-ray beam energy, the site of interest in the object is properly selected through the weighting process and image subtraction process.

Then, the 3D reconstruction device carries out a 3D reconstruction process, based on a large number of subtraction images repeatedly acquired by the energy subtraction device, to acquire a 3D X-ray image selectively showing the site of interest in the object under examination. The large number plurality of subtraction images acquired by the energy difference using subtraction device reflect different rotational phases of the X-ray beam irradiation device and the two-dimensional X-ray detecting device, and are images picked up from various directions of the site of interest in the object under examination. Thus, a 3D X-ray image can be acquired through the 3D reconstruction process based on the pixel signals of the subtraction images and the rotational phases of the X-ray beam emitting device and the two-dimensional X-ray detecting device which are geometric positions of the subtraction images.

Thus, with the X-ray imaging apparatus according to the invention in the first embodiment, the subtraction images obtained by the energy difference using subtraction device serve as the basis for the 3D reconstruction process for acquiring a 3D X-ray image selectively showing the site of interest in the object under examination. In addition, as a result of the image subtraction process carried out by the energy difference using subtraction device on the high energy X-ray photo images and low energy X-ray photo images according to the appropriate weights set by the weight setting device to the high and low energy X-ray photo images, the subtraction images obtained by the energy difference using subtraction device selects only the site of interest in the object under examination, and eliminates the background around the site of interest.

Thus, even if body motion should occur with in the background around the site of interest of the object under examination while a large number of subtraction images are acquired one after another by the energy difference using subtraction device, the body motion of the object would never appear on the subtraction images, or on the 3D X-ray image acquired on the basis of the subtraction images, because the background is eliminated from each subtraction image.

Therefore, the X-ray imaging apparatus according to the invention in the first embodiment can prevent artifacts due to body motion of the object under examination from appears in the 3D X-ray image selectively showing the site of interest in the object under examination.

An X-ray imaging apparatus according to the invention defined in the second embodiment is characterized by comprising (A) an X-ray beam emitting device for emitting X-ray beams to an object under examination to be radiographed; (B) a two-dimensional X-ray detecting device for detecting transmitted X-ray images of the object under examination produced by emission of the X-ray beams to the object under examination, and outputting X-ray detection signals in real time; (C) a revolution device for revolving the X-ray beam emitting device and the two-dimensional X-ray detecting device about the object under examination as opposed to each other with the object under examination in between; (D) an X-ray energy switching control device for performing X-ray energy switching control to switch the X-ray beams emitted from the X-ray beam emitting device alternately to high energy X-ray beams of high energy and to low energy X-ray beams of low energy; (E) a high energy image acquiring device for acquiring high energy X-ray photo images based on X-ray detection signals outputted from the two-dimensional X-ray detecting device as a result of emission of the high energy X-ray beams; (F) a low energy image acquiring device for acquiring low energy X-ray photo images based on X-ray detection signals outputted from the two-dimensional X-ray detecting device as a result of emission of the low energy X-ray beams; (J) a 3D reconstruction device for carrying out a 3D reconstruction process based on the high energy X-ray photo images to acquire a 3D X-ray image of high energy X-ray radiography, and a 3D reconstruction process based on the low energy X-ray photo images to acquire a 3D X-ray image of low energy X-ray radiography; (K) a weight setting device for setting weights suitable for selecting a site of interest in the object under examination with respect to the 3D X-ray image of high energy X-ray radiography and 3D X-ray image of low energy X-ray radiography; and (L) an energy difference using subtraction device for acquiring a 3D subtraction image through an image subtraction process carried out, according to the weights set by the weight setting device, on the 3D X-ray image of high energy X-ray radiography and 3D X-ray image of low energy X-ray radiography.

[Functions and Effects] While the X-ray beam emitting device and the two-dimensional X-ray detecting device are revolved about the object under examination by the revolution device, the X-ray beam emitting device, under the X-ray energy switching control from the X-ray energy switching control device, repeatedly irradiates the object with a high energy X-ray beam having high energy and a low energy X-ray beam having low energy in alternation. In parallel with this, the two-dimensional X-ray detecting device detects a transmitted X-ray image of the object produced whenever the high energy X-ray beam or the low energy X-ray beam having low energy is emitted to the object, and outputs X-ray detection signals in real time.

When both the high and low energy X-ray photo images about the object under examination have been collected, the 3D reconstruction device carries out a 3D reconstruction process based on the high energy X-ray photo images to acquire a 3D X-ray image of high energy X-ray radiography, and similarly carries out a 3D reconstruction process based on the low energy X-ray photo images to acquire a 3D X-ray image of low energy X-ray radiography. Next, an image subtraction process is carried out on the 3D image of high energy X-ray radiography and the 3D image of low energy X-ray radiography according to the weights set by the weighting setting device, to acquire a 3D subtraction image.

As described above, the invention defined in the second embodiment obtains a 3D subtraction image by carrying out a 3D reconstruction process separately on the high energy X-ray photo images and on the low energy X-ray photo images, and thereafter carrying out a weighted subtraction process on the 3D image of high energy X-ray radiography and the 3D image of low energy X-ray radiography. Since the 3D reconstruction process is carried out directly on the high energy X-ray photo images and low energy X-ray photo images, artifacts due to displacement are not produced unlike the case of using subtraction images in the reconstruction process. Since the weighted subtraction process is carried out after the 3D reconstruction process, the 3D reconstruction process imposing a heavy processing burden need not be done all over again even when weighting factors are changed. Therefore, according to the invention defined in the second embodiment, the weighting factors can be changed to set optimal factors at will, thereby realizing a high-quality 3D subtraction image.

The invention in the third embodiment provides an X-ray imaging apparatus as defined in the first embodiment or the second embodiment, comprising a contrast medium using subtraction device for acquiring a subtraction image selecting a contrast medium injected site through an image subtraction process carried out on images of the object under examination before a contrast medium is injected and on images of the object under examination after the contrast medium is injected.

[Functions and Effects] With the X-ray imaging apparatus in the third embodiment, the contrast medium injected site is selected by the contrast medium using subtraction device which carries out an image subtraction process on images of the object under examination before a contrast medium is injected and on images of the object under examination after the contrast medium is injected.

The invention in the fourth embodiment provides an X-ray imaging apparatus as defined in the third embodiment, wherein the contrast medium using subtraction device carries out the image subtraction process on the subtraction images, acquired by the energy subtraction device, of the object under examination before and after the contrast medium is injected, respectively, and the 3D reconstruction device carries out the 3D reconstruction process using the subtraction images acquired by the contrast medium using subtraction device.

[Functions and Effects] With the X-ray imaging apparatus in the fourth embodiment, the contrast medium using subtraction device carries out the image subtraction process on the subtraction images, acquired by the energy subtraction device, of the object under examination before and after the contrast medium is injected, respectively. The 3D reconstruction device carries out the 3D reconstruction process to acquire a 3D X-ray image selecting the contrast medium injected site as the site of interest of the object under examination, from the subtraction images acquired by the contrast medium using subtraction device.

The invention in the fifth embodiment provides an X-ray imaging apparatus as defined in the first embodiment or the second embodiment, wherein the X-ray beam emitting device and the two-dimensional X-ray detecting device are attached separately to one end and the other end of a C-shaped arm to be opposed to each other.

[Functions and Effects] With the X-ray imaging apparatus in the fifth embodiment, since the X-ray beam emitting device and the two-dimensional X-ray detecting device are attached separately to one end and the other end of a C-shaped arm, the X-ray beam emitting device and the two-dimensional X-ray detecting device may easily be revolved around the object under examination as opposed to each other.

The invention in the sixth embodiment provides an X-ray imaging apparatus as defined in the fifth embodiment, wherein a revolution device revolves the X-ray beam emitting device and the two-dimensional X-ray detecting device through at least 180 degrees about the object under examination.

[Functions and Effects] With the X-ray imaging apparatus in the sixth embodiment, the revolution device revolves the X-ray beam emitting device and the two-dimensional X-ray detecting device through at least 180 degrees about the object under examination. Since the subtraction images serving as the basis for the 3D reconstruction process for acquiring a 3D X-ray image are obtained over a large range of 180 degrees or more, the 3D reconstruction process for acquiring a 3D X-ray image may be carried out with high precision.

The invention in the seventh embodiment provides an X-ray imaging apparatus as defined in the sixth embodiment, wherein the revolution device drives the X-ray beam emitting device and the two-dimensional X-ray detecting device for accelerated revolution, uniform speed revolution and decelerated revolution in order, the X-ray beams being emitted while the X-ray beam emitting device and the two-dimensional X-ray detecting device are driven for the uniform speed revolution.

[Functions and Effects] The X-ray imaging apparatus in the seventh embodiment provides a stage of accelerated revolution and a stage of decelerated revolution before and after the uniform speed revolution of the X-ray beam emitting device and the two-dimensional X-ray detecting device. Thus, the X-ray beam emitting device and the two-dimensional X-ray detecting device may shift smoothly to the stage of uniform speed revolution for X-ray emission.

The invention in the eighth embodiment provides an X-ray imaging apparatus as defined in the first embodiment or the second embodiment, wherein the X-ray energy switching control device applies a high voltage to the X-ray beam emitting device to emit the high energy X-ray beams of high energy, and applies a low voltage to the X-ray beam emitting device to emit the low energy X-ray beams of low energy.

[Functions and Effects] The X-ray imaging apparatus according to the invention in the eighth embodiment can obtain the high energy X-ray beams and low energy X-ray beams by switching the voltage to the X-ray beam emitting device between a high voltage and a low voltage in alternation.

The invention in the ninth embodiment provides an X-ray imaging apparatus as defined in the first embodiment or the second embodiment, wherein the X-ray energy switching control device causes the X-ray beams emitted from the X-ray beam emitting device to pass through a low energy absorbing member, thereby to emit the high energy X-ray beams of high energy, and causes the X-ray beams emitted from the X-ray beam emitting device to pass through a high energy absorbing member, thereby to emit the low energy X-ray beams of low energy.

[Functions and Effects] The X-ray imaging apparatus according to the invention in the ninth embodiment can obtain the high energy X-ray beams and low energy X-ray beams by causing the X-ray beams emitted from the X-ray beam emitting device to pass alternately through the low energy absorbing member and the high energy absorbing member.

EFFECTS OF THE INVENTION

With the X-ray imaging apparatus according to the invention in the first embodiment, the subtraction images obtained by the energy difference using subtraction device serve as the basis for the 3D reconstruction process for acquiring a 3D X-ray image selectively showing the site of interest in the object under examination. In addition, as a result of the image subtraction process carried out by the energy difference using subtraction device on the high energy X-ray photo images and low energy X-ray photo images according to the appropriate weights set by the weight setting device to the high and low energy X-ray photo images, the subtraction images obtained by the energy difference using subtraction device selects only the site of interest in the object under examination, and eliminates the background around the site of interest.

Thus, even if body motion should occur with in the background around the site of interest of the object under examination while a large number of subtraction images are acquired one after another by the energy difference using subtraction device, the body motion of the object would never appear on the subtraction images, or on the 3D X-ray image acquired on the basis of the subtraction images, because the background is eliminated from each subtraction image.

Therefore, the X-ray imaging apparatus according to the invention in the first embodiment can prevent artifacts due to body motion of the object under examination from appears in the 3D X-ray image selectively showing the site of interest in the object under examination.

The X-ray imaging apparatus according to the invention in the second embodiment obtains a 3D subtraction image by carrying out a 3D reconstruction process separately on the high energy X-ray photo images and on the low energy X-ray photo images, and thereafter carrying out a weighted subtraction process on the 3D image of high energy X-ray radiography and the 3D image of low energy X-ray radiography. Therefore, artifacts due to displacement are hardly produced in the reconstruction process. Further, according to the invention defined in the second embodiment, the weighting factors can be changed to set optimal factors at will, thereby realizing a high-quality 3D subtraction image.

Schematic view showing an example of 3D X-ray image acquired by a 3D reconstruction unit of the apparatus in the first embodiment

FIG. 18

Block diagram showing an overall construction of an X-ray imaging apparatus in a second embodiment

FIG. 19

Flow chart showing a process of obtaining a 3D X-ray image by the apparatus in the second embodiment

FIG. 20

Explanatory view of another embodiment of an energy switching control device

DESCRIPTION OF REFERENCES

1 ... X-ray tube (X-ray beam emitting device)
2 ... FPD (two-dimensional X-ray detecting device)
3 ... revolution mechanism (revolution device)
8 ... X-ray energy switching control unit (X-ray energy switchover control device)
10 ... high energy image acquiring unit (high energy image acquiring device)
11 ... low energy image acquiring unit (low energy image acquiring device)
14 ... weight setter (weight setting device)
15 ... energy subtraction unit (energy difference using subtraction device)
18 ... contrast medium selecting subtraction unit (contrast medium using subtraction device)
20 ... 3D reconstruction unit (3D reconstruction device)
M ... patient
P1 ... subtraction image
P2 ... subtraction image
P3 ... subtraction image
P4 ... 3D X-ray image
R ... blood vessels (site of interest)
XA ... X-ray beam Embodiment 1

Figure 1:
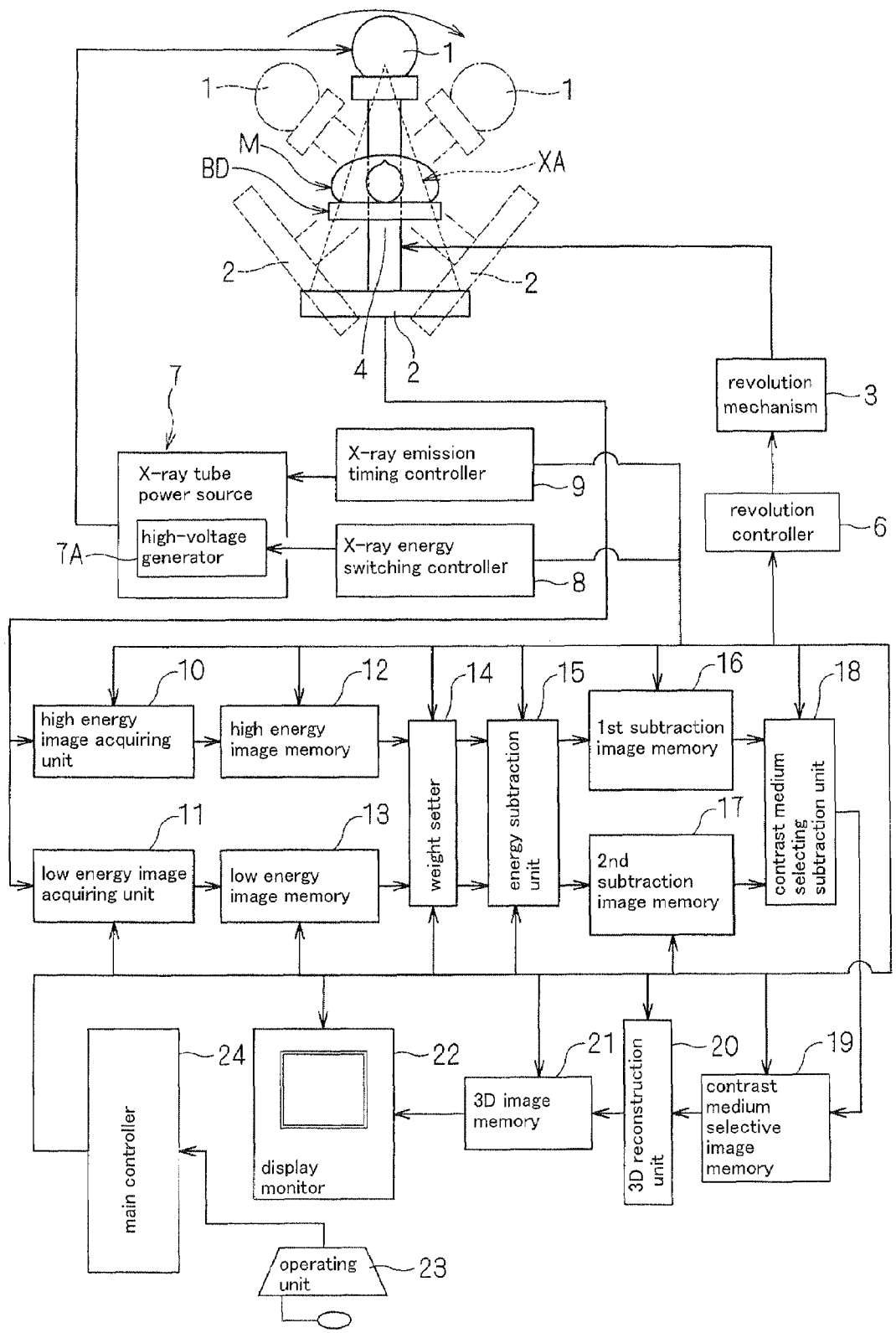
FIG. 1
Block diagram showing an overall construction of an X-ray imaging apparatus in a first embodiment FIG. 2
Elevational view showing a construction of an X-ray imaging system of the X-ray imaging apparatus in the first embodiment FIG. 3
Schematic view showing a rotation range of an X-ray tube and an FPD of the X-ray imaging apparatus in the first embodiment FIG. 4
Graph showing a situation of voltage application to the X-ray tube versus an output situation of X-ray detection signals from the FPD of the X-ray imaging apparatus in the first embodiment FIG. 5
Block diagram showing details of a 3D image reconstruction unit of the X-ray imaging apparatus in the first embodiment FIG. 6
(a) is a schematic side view showing one scan mode of the X-ray tube and FPD in the X-ray imaging apparatus in the first embodiment, and (b) is a schematic perspective view of (a).
Figure 2:
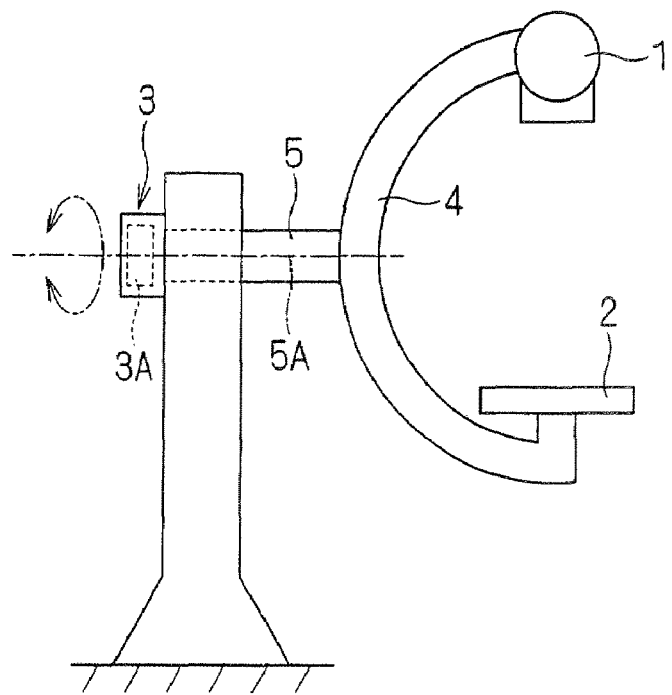

A first embodiment of the X-ray imaging apparatus of this invention will be described. FIG. 1 is a block diagram showing an overall construction of the X-ray imaging apparatus in the embodiment which can carry out angiography (angiographic examination). FIG. 2 is an elevational view showing a construction of an X-ray imaging system of the X-ray imaging apparatus in the embodiment.

As shown in FIG. 1, the X-ray imaging apparatus in the first embodiment includes an X-ray tube 1 acting as an X-ray beam emitting device for emitting an X-ray beam XA in the form of a cone to a patient M placed on a top board BD to be radiographed, a flat panel X-ray detector (hereinafter abbreviated as "FPD" where appropriate) 2 acting as a two-dimensional X-ray detecting device for detecting transmitted X-ray images of the patient M produced by emission of the X-ray beam XA to the patient M, and outputting X-ray detection signals, and a revolution mechanism 3 for revolving the X-ray tube 1 and FPD 2 around the patient M as opposed to each other across the patient M.

As shown in FIG. 2, the X-ray tube 1 and FPD 2 are attached to one end and the other end of a C-shaped arm 4 supported by a support shaft member 5. The revolution mechanism 3 has an electric motor 3A for rotating the support shaft member 5 about a central axis 5A serving as a rotational axis. The C-shaped arm 4 rotates as the revolution mechanism 3 turns the electric motor 3A to rotate the support shaft member 5. With rotation of the C-shaped arm 4, the X-ray tube 1 and FPD 2 revolve around the patient M.

Figure 3:
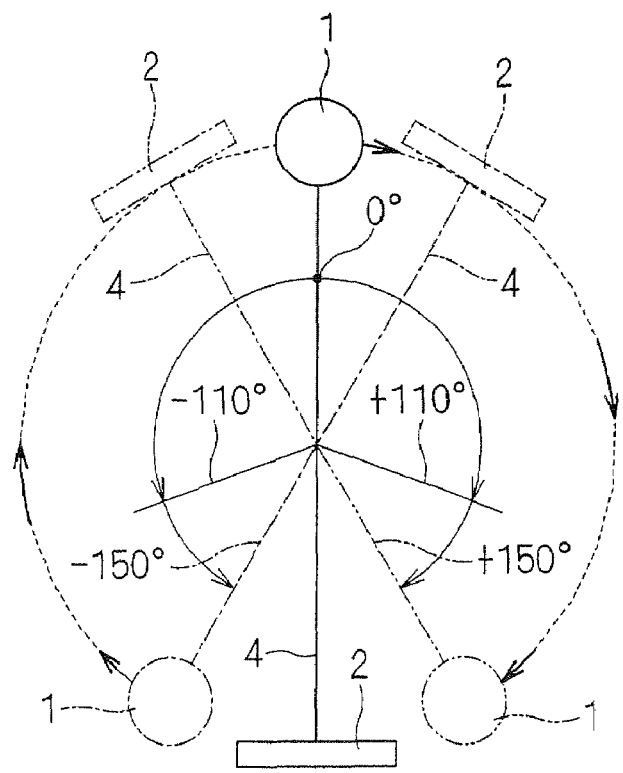

In the case of the apparatus in this embodiment, as shown in FIG. 3, the revolution mechanism 3 revolves the X-ray tube 1 and FPD 2 over a maximum angular range of 300° from −150° to +150°, under revolving speed control by a revolution controller 6. The X-ray tube 1 and FPD 2 are revolvable at a uniform speed over a maximum range of −110° to +110°. Besides, an accelerated revolution period from −150° to −110° is provided before attaining the uniform speed at −110°, and a decelerated revolution period from +110° to +150° is provided after the uniform speed at +110° until the revolution is stopped. While the X-ray tube 1 and FPD 2 revolve at the uniform speed, X-ray photography progresses with emission of X-ray beams. The uniform revolution range of the X-ray tube 1 and FPD 2 may be set to a range smaller than −110° to +110°.

Figure 4A:
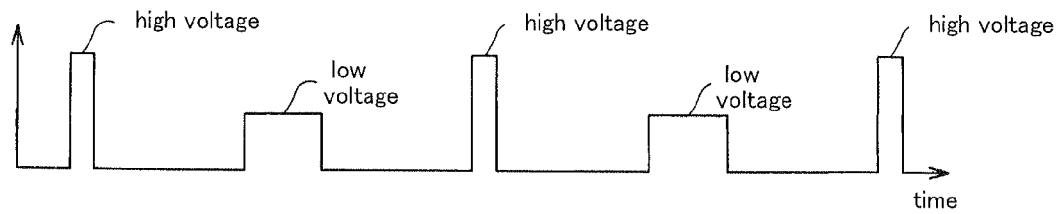
Figure 4B:
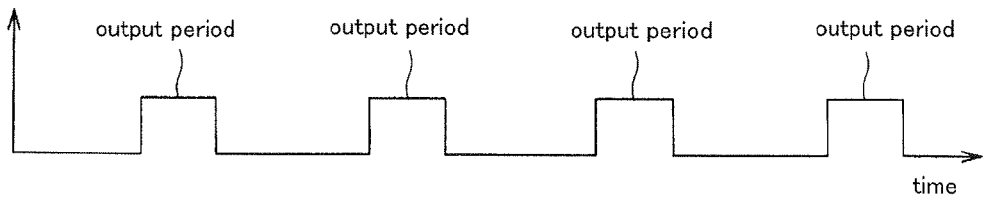

On the other hand, the X-ray tube 1 emits the X-ray beam XA whenever driving electric power is supplied from an X-ray tube power source 7. The apparatus in this embodiment has an X-ray energy switching controller 8 for performing X-ray energy switching control to switch, back and forth, the X-ray beam XA emitted from the X-ray tube 1 between a high energy X-ray beam having high energy and a low energy X-ray beam having low energy. Specifically, as shown in FIG. 4 (a), the X-ray energy switching controller 8 performs X-ray energy switching control by switching, back and forth, a high voltage of a high-voltage generator 7A of the X-ray tube power source 7 between a high voltage for a high energy X-ray beam (e.g. 140 kV) and a low voltage for a low energy X-ray beam (e.g. 60 kV).

In addition, the apparatus in this embodiment has an X-ray emission timing controller 9 for performing emission timing control for causing the X-ray tube 1 to emit one X-ray beam XA after another when the X-ray tube 1 and FPD 2 reach predetermined revolutional phases. For example, the X-ray tube 1 emits an X-ray beam at a time of the −110° angle (revolutional phase) as first emission timing, thereafter emits an X-ray beam in each fixed revolutional phase (whenever it revolves through a fixed angle), and emits an X-ray beam at a time of the +110° angle (rotational phase) as last emission timing. Thus, the emission timing control by the X-ray emission timing controller 9 and the X-ray energy switching control by the X-ray energy switching controller 8 are carried out synchronously. Where the uniform revolution range of the X-ray tube 1 and FPD 2 is set to a range smaller than −110° to +110°, the first and last emission timings will change according to the set uniform revolution range.

That is, in the apparatus in this embodiment, while the X-ray tube 1 and FPD 2 opposed to each other across the patient M are revolved about the patient M by the revolution mechanism 3, the X-ray tube 1, under the X-ray energy switching control from the X-ray energy switching controller 8 and the emission timing control from the X-ray emission timing controller 9, repeatedly irradiates the patient with a high energy X-ray beam having high energy and a low energy X-ray beam having low energy in alternation. In parallel with this, the FPD 2 detects a transmitted X-ray image of the patient M produced whenever the high energy X-ray beam or the low energy X-ray beam having low energy is emitted to the patient M, and outputs X-ray detection signals in real time as shown in FIG. 4 (b).

On the other hand, the apparatus in this embodiment has a high energy image acquiring unit 10 for acquiring high energy X-ray photo images based on the X-ray detection signals outputted from the FPD 2 with emission of the high energy X-ray beams, and sending these images to a high energy image memory 12, and a low energy image acquiring unit 11 for acquiring low energy X-ray photo images based on the X-ray detection signals outputted from the FPD 2 with emission of the low energy X-ray beams, and sending these images to a low energy image memory 13.

Further, the apparatus in this embodiment has a weight setter 14 for setting suitable weights to select a site of interest in the patient with respect to the high energy X-ray photo images and low energy X-ray photo images, and an energy subtraction unit (energy difference using type subtraction device) 15 for acquiring a subtraction image by carrying out an image subtraction process, based on the weights set by the weight setter 14, of a high energy X-ray photo image and a low energy X-ray photo image acquired as adjacent each other in time.

Specifically, the weight setter 14 sets factor a to the high energy X-ray photo images, and factor b to the low energy X-ray photo images. The energy subtraction unit 15 carries out an image subtraction operation, a×log (pixel signals of the high energy X-ray photo images)−b×log (pixel signals of the low energy X-ray photo images). Therefore, by suitably adjusting factor a and factor b set by the weight setter 14, images showing substantially only osseous parts such as the ribs or backbone, for example, can be acquired as subtraction images. It is of course possible, through adjustment of factor a and factor b, to acquire images showing substantially only soft tissue as subtraction images.

The high energy X-ray photo image and low energy X-ray photo image acquired as adjacent each other in time are photographed at substantially the same time. Since the high energy X-ray photo image and low energy X-ray photo image are different only in X-ray beam energy, a site of interest in the patient M is properly selected through the image subtraction process by the energy subtraction unit 15.

Usually, immediately after the high energy X-ray photo image is photographed, the low energy X-ray photo image is acquired. Thus, one subtraction image is acquired after another from such pairs of the high energy X-ray photo image and low energy X-ray photo image. However, when the high energy X-ray photo image is acquired immediately after the low energy X-ray photo image, one subtraction image is acquired after another also from such pairs of the low energy X-ray photo image and high energy X-ray photo image. In the latter case, subtraction images are acquired in about twice the number in the former.

A first subtraction image memory 16 and a second subtraction image memory 17 are arranged downstream of the energy subtraction unit 15. When angiography is carried out by the apparatus in this embodiment, subtraction images acquired by the energy subtraction unit 15 before contrast medium injection are stored in the first subtraction image memory 16, and subtraction images acquired by the energy subtraction unit 15 after contrast medium injection are stored in the second subtraction image memory 17.

The apparatus in this embodiment has a contrast medium selecting subtraction unit (contrast medium using subtraction device) 18 for carrying out an image subtraction process on subtraction images of the patient M before the contrast medium is injected and subtraction images of the patient M after the contrast medium is injected to acquire subtraction images selecting a site into which the contrast medium is injected, and store the subtraction images in a contrast medium selective image memory 19.

Specifically, the contrast medium selecting subtraction unit 18 carries out an image subtraction process by superimposing subtraction images of the same rotational phase stored in the first subtraction image memory 16 and second subtraction image memory 17, to acquire one subtraction image after another in which the contrast medium injected site is selected.

The apparatus in this embodiment further includes a 3D reconstruction unit 20 for carrying out a 3D reconstruction process using numerous subtraction images stored in the contrast medium selective image memory 19 to acquire a 3D X-ray image in which the contrast medium injected site is selected and shown as a site of interest in the patient M. The 3D reconstruction unit 20 acquires the 3D X-ray image directly from the subtraction images acquired by the contrast medium selecting subtraction unit 18. The subtraction images acquired by the contrast medium selecting subtraction unit 18 arc the subtraction images acquired by the energy subtraction unit 15. Thus, the 3D reconstruction unit 20 always carries out the 3D reconstruction process on the basis of the subtraction images acquired by the energy subtraction unit 15.

The numerous subtraction images stored in the contrast medium selective image memory 19 reflect different rotational phases of the X-ray tube 1 and FPD 2, and are images picked up from various directions of the contrast medium injected site as a site of interest in the patient M. Thus, the 3D reconstruction unit 20 carries out the 3D reconstruction process based on the pixel signals of the subtraction images and the rotational phases of the X-ray tube 1 and FPD 2 which are geometric positions of the subtraction images, to acquire a 3D X-ray image selectively showing the contrast medium injected site as a site of interest in the patient M.

Figure 5:
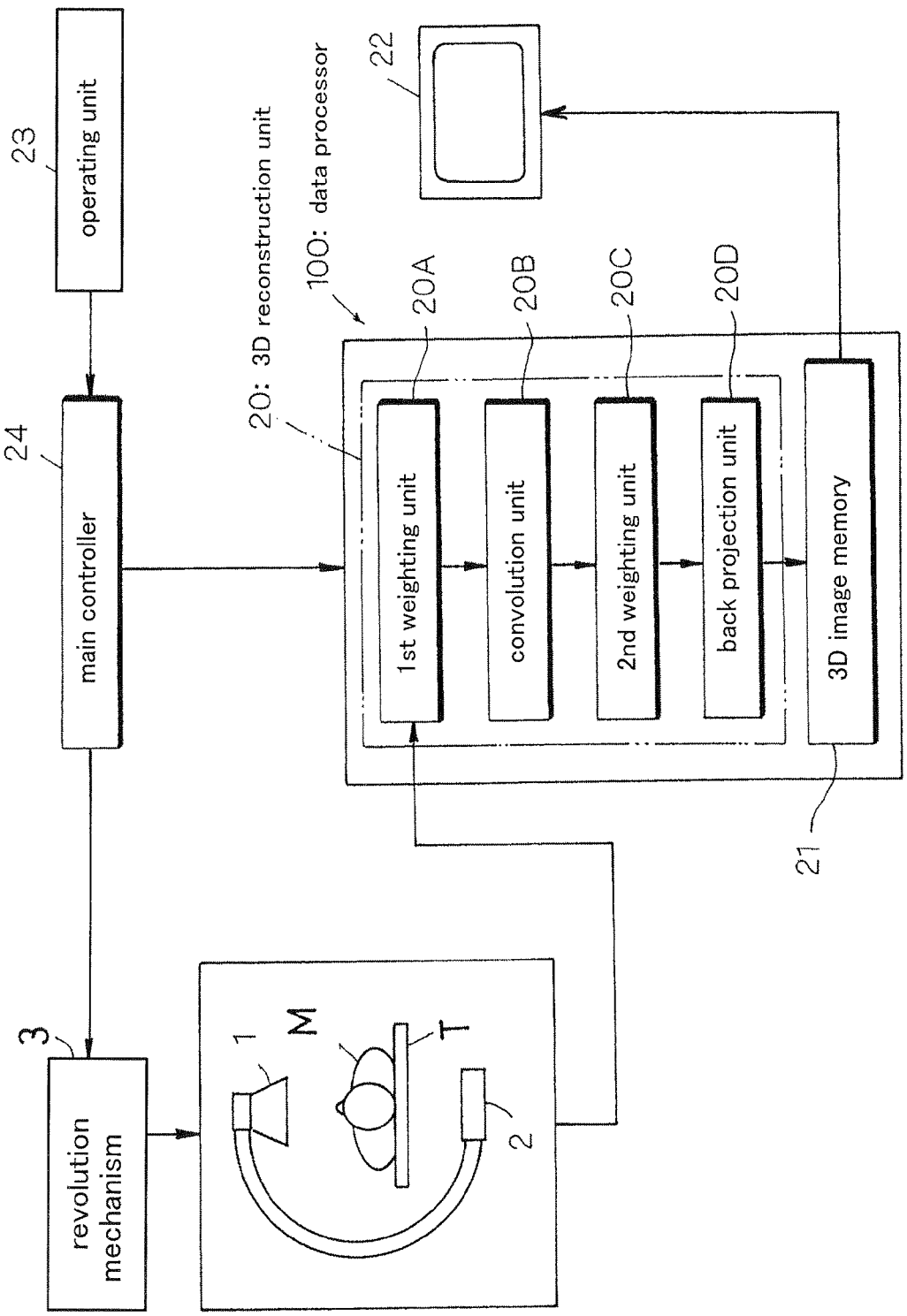
Figure 6A:
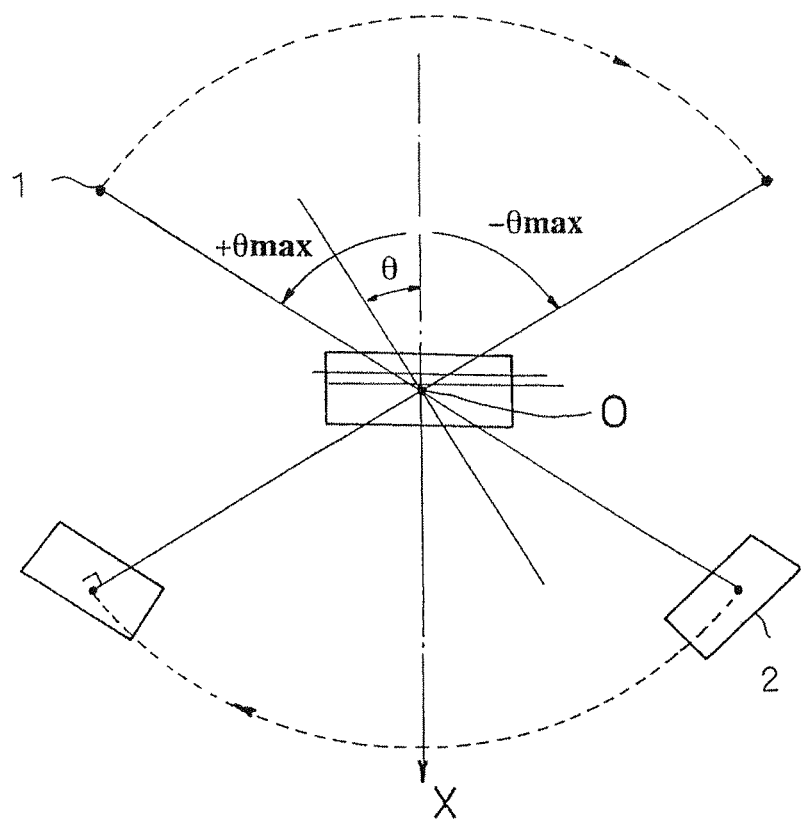
Figure 6B:
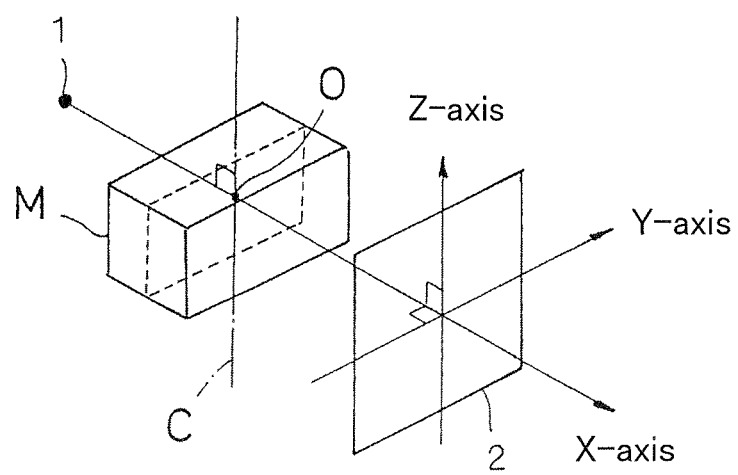

A series of procedures of image reconstruction for generating 3D volume data of a site of interest based on the Feldkamp method as an example of specific algorithm for acquiring a 3D X-ray image will now be outlined with reference to FIGS. 5 and 6. First, as shown in FIG. 6, two arcuate tracks are set, opposed to each other across the patient M, on a circumferential track around a central axis of revolution C set substantially centrally of the site of interest of the patient M. The X-ray tube 1 is moved on one of the arcuate tracks, and the flat panel X-ray detector (FPD) 2 is moved on the other arcuate track in synchronism therewith to maintain a fixed distance from the X-ray tube 1 to perform arcuate scanning for picking up images of the site of interest of the patient M. This operation acquires a group of projection data of the site of interest of the patient M detected in varied scan positions. Next, the projection data are individually subjected to a first weighting process described hereinafter. Then, a predetermined convolution process described hereinafter is performed on the projection data resulting from the first weighting process. Next, a second weighting process described hereinafter is performed on the projection data resulting from the convolution process. Next, the projection data resulting from the second weighting process are individually subjected to a predetermined back projection (BP) to be described hereinafter, to generate a BP image (3D volume data). In this way, an image reconstruction is carried out to generate 3D volume data of the site of interest. The operator may observe an image of any sectional plane (seen in the direction of an X-axis) selected from the 3D volume data.

Figure 7:
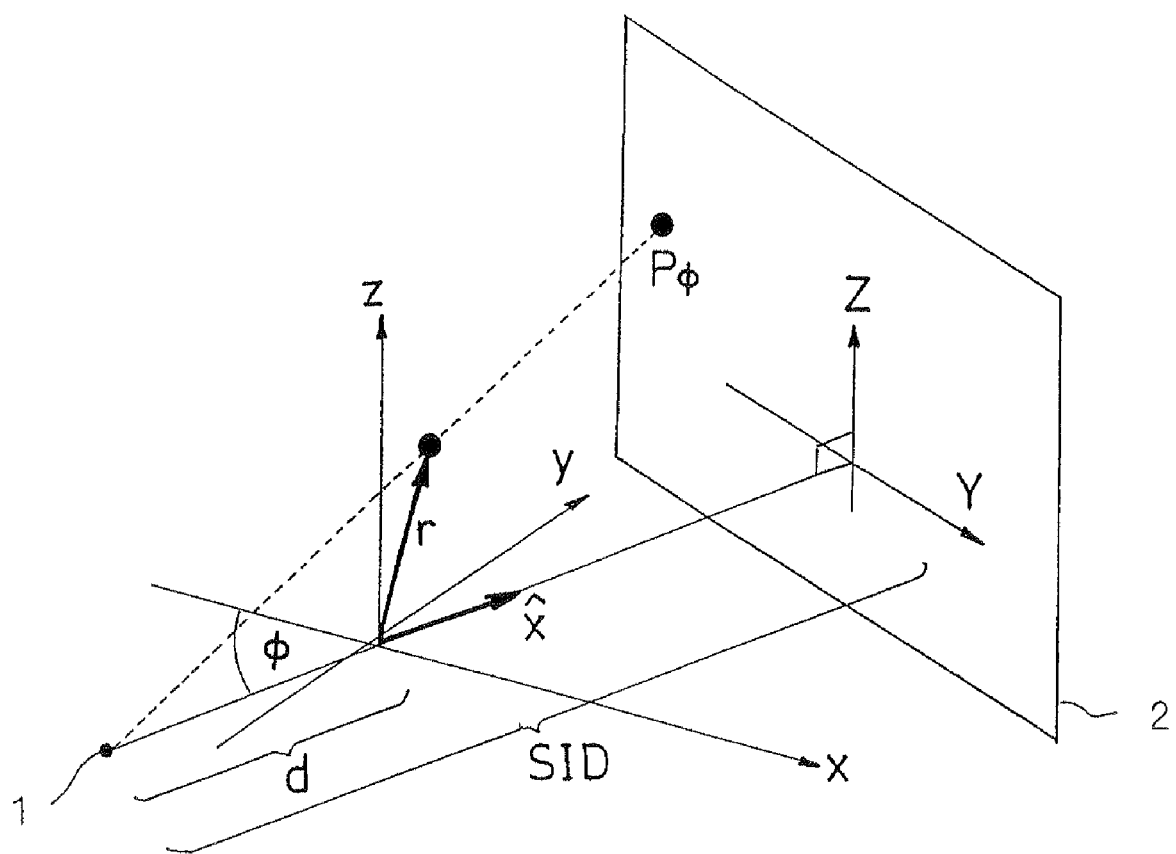
FIG. 7
Schematic view illustrating Feldkamp algorithm according to the first embodiment.

The above algorithm of Feldkamp is expressed by the following equation (1)-equation (3). A cube f (r) is reconstructed based on a plurality of projection data $P\phi$ from different angles (see FIG. 7).

To calculate a CT value strictly, it is necessary to carry out a correction beforehand for substituting water equivalency for projection data $P\phi$.

[Math 1]

$$f(\vec{r}) = \frac{1}{4\pi^2} \oint W_2 \underbrace{\int_{-\infty}^{\infty} g_y(Y(\vec{r})-Y')P_\phi(Y',Z(\vec{r}))W_1 \, dY'}_{\text{convolution}} \, d\Phi \quad (1)$$

correction of influence of beam divergence back projection $$W_1 = \frac{d}{\sqrt{d+Y'^2+Z^2}} \quad (2)$$

$$W_2 = \frac{d^2}{(d+\vec{r}\cdot\hat{x}')^2} \quad (3)$$

Here, f(r) is pixel data for position r of the cube (3D volume data) to be reconstructed. Y (vr) and Z (vr) are coordinates of a point where the pixel of position r is projected on the detecting plane of FPD 2. The above small letter v means "vector", and vector will be represented hereinafter by small letter "v" as appropriate. Pϕ is projection data on the detecting plane of FPD 2 at projection angle ϕ. Gy is called the filter function of Filtered Back Projection, and is |ω| (absolute value omega) filter function described hereinafter. $W_1$ and $W_2$ are factors for correcting the influence of beam divergence. $W_1$ is a factor relating to a first weighting process described hereinafter. $W_2$ is a factor relating to a second weighting process described hereinafter.

As shown in FIG. 5, a data processor 100 includes a 3D reconstruction unit 20 and a 3D image memory 21. Here, the construction relating to the energy subtraction shown in FIG. 1 is omitted. The 3D reconstruction unit 20 includes a first weighting unit 20A for performing the first weighting process individually on the group of subtraction images (i.e. projection data resulting from the subtraction process: hereinafter called simply "projection data") stored in the contrast medium selective image memory 19 shown in FIG. 1 (which is omitted from FIG. 5), a convolution unit 20B for performing the predetermined convolution process on each projection data after the first weighting process, a second weighting unit 20C for performing the second weighting process on each projection data after the convolution process, and a back projection unit 20D for performing the predetermined back projection (BP) individually of the projection data after the second weighting process to generate a BP image (3D volume data).

Figure 8:
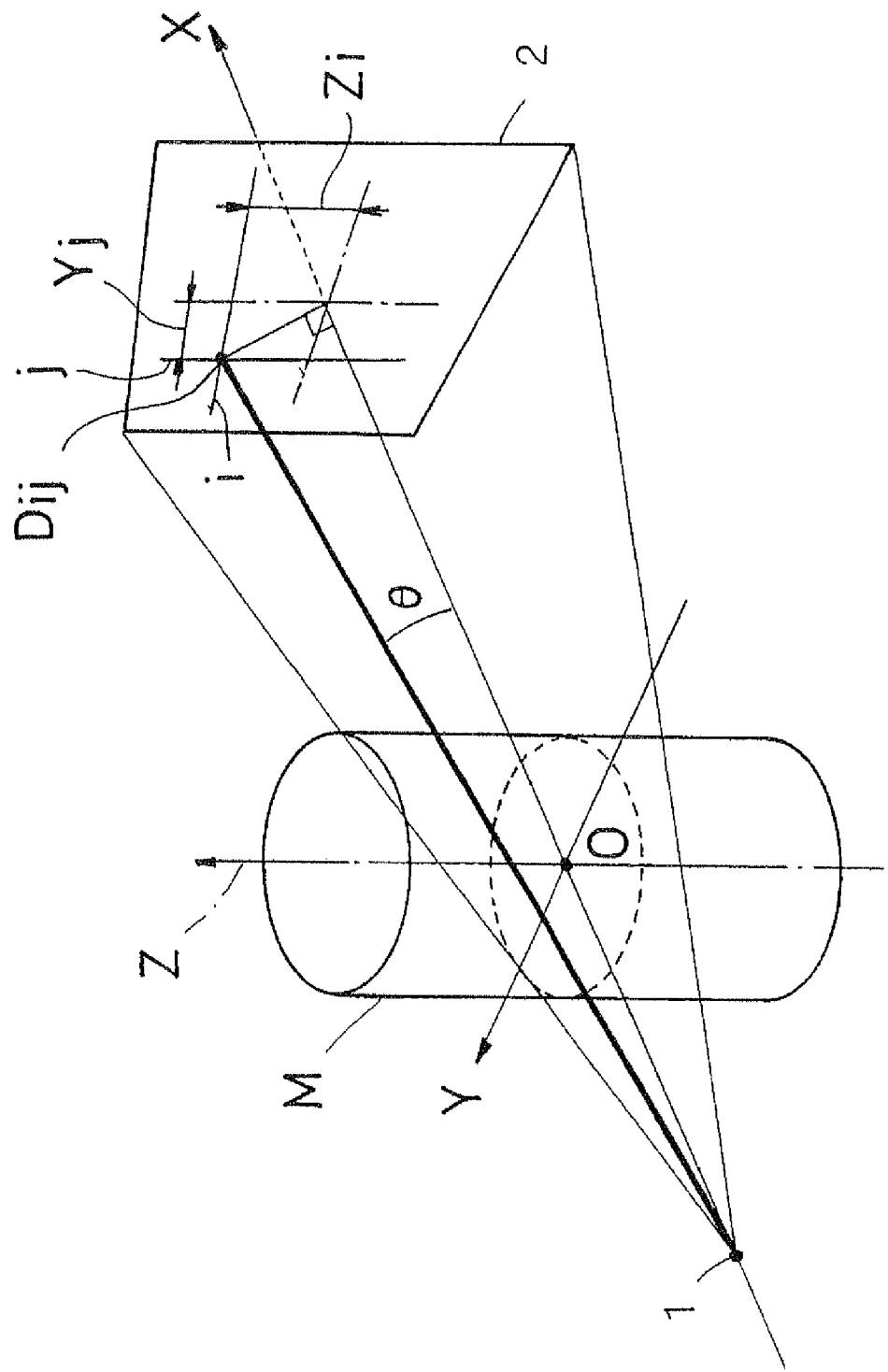
FIG. 8
Schematic view illustrating a cosine correction by a first weighting unit in the first embodiment FIG. 9
Schematic view illustrating a series of processes in a convolution unit in the first embodiment FIG. 10
(a) and (b) are characteristic views showing each filter function of a filtering unit in the first embodiment FIG. 11
Schematic view illustrating for describing a process of back projection to an imaginary 3D lattice group of projection data after a convolution process FIG. 12
Schematic view illustrating for describing a process of back projection to an imaginary 3D lattice group of projection data after a convolution process FIG. 13
Flow chart showing a process of obtaining a 3D X-ray image by the apparatus in the first embodiment FIG. 14
Schematic view showing an example of subtraction images obtained from an energy subtraction unit of the apparatus in the embodiment FIG. 15
Schematic view showing another example of subtraction images obtained from the energy subtraction unit of the apparatus in the first embodiment FIG. 16
Schematic view showing an example of subtraction images obtained from a contrast medium selecting subtraction unit of the apparatus in the first embodiment

The first weighting unit 20A performs the first weighting process individually on the group of projection data acquired by radiography. Specifically, as shown in FIG. 8, pixel detection level fluctuations in the viewing direction are corrected one pixel row i after another of the FPD 2, for projection data detected in varied scan positions by the FPD 3. As shown in FIG. 8, the center point of X rays emitted in the form of a cone beam from the X-ray tube 1 toward the patient M always passes through the center point O of a particular sectional plane of patient M (which is also a point on the central axis of revolution C), and impinges on the center point of the detecting plane of FPD 2 in a direction perpendicular thereto.

Then, as shown in FIG. 8, the first weighting unit 20A performs, on the projection data, a weighting process based on the following equation (4):

$$\cos\theta = SID/(SID^2+Yj^2+Zj^2)^{1/2} \quad (4)$$

That is, the weighting process is performed by multiplying each pixel by cos θ of equation (4). For example, a weighted value of pixel Dij is derived from Yj·cos θ. This is fixed regardless of the views, and therefore is provided beforehand for the weighting process. In this way, projection data after the first weighting process is calculated (FIG. 9 shows this as "projection image after the first weighting process: SC (i, j)").

The convolution unit 20B performs the predetermined convolution process on each projection data after the first weighting process, i.e. the projection image after the first weighting process: SC (i, j). The convolution process performed in the real space is equivalent to a filtering process in the Fourier space. Thus, for expediency of description, the above predetermined convolution process will be described as filtering processes performed in the Fourier space (|ω| filtering (absolute value omega) filtering process shown in FIG. 9). The |ω| filtering process performed by the convolution unit 20B will be described hereinafter.

The convolution unit 20B includes a one-dimensional Fourier transform unit for performing a one-dimensional Fourier transform sideways on each i-row of FPD 2 to generate an image in Fourier space SCF (i, ω), an |ω| filtering unit for applying an |ω| filter to the image in Fourier space SCF (i, ω) resulting from the one-dimensional Fourier transform, and a one-dimensional inverse Fourier transform unit for performing a one-dimensional inverse Fourier transform of the image in Fourier space SCF (i, ω) |ω|-filtered by the |ω| filtering unit to put the image back to real space data.

As shown in FIG. 9, the filtering unit includes an |ω| filtering unit having a filter for suppressing high frequency noise by isotropically reducing the high frequency regions in the i-direction of the image in Fourier space SCF (i, ω) resulting from the one-dimensional Fourier transform, and a filter dependent on a data collection scan mode. The filter dependent on a data collecting scan mode suppresses DC components to reduce artifacts caused by the DC components being emphasized, when the filtered image in Fourier space SCF' (i, ω) is subjected to the one-dimensional inverse Fourier transform.

The meaning of the filtering process performed in the one-dimensional Fourier space will be described now. The filtering process performed in the one-dimensional Fourier space is mathematically expressed by the following equation (5):

$$SCF'(i,\omega) = SCF(i,\omega) \times M(\omega i) \quad (5)$$

where SCF' (i, ω) is the filtered one-dimensional image in Fourier space, and M (ωi) is a function representing filter characteristics of the above filtering unit.

M (ωi) is expressed by the following equation (6) as a product of two functions representing the filter characteristics:

$$M(\omega i) = Mi(\omega i) \cdot M\omega(\omega i) \quad (6)$$

A typical example of each filter function system shown in the equation (6) will be described hereinafter.

Figure 10A:
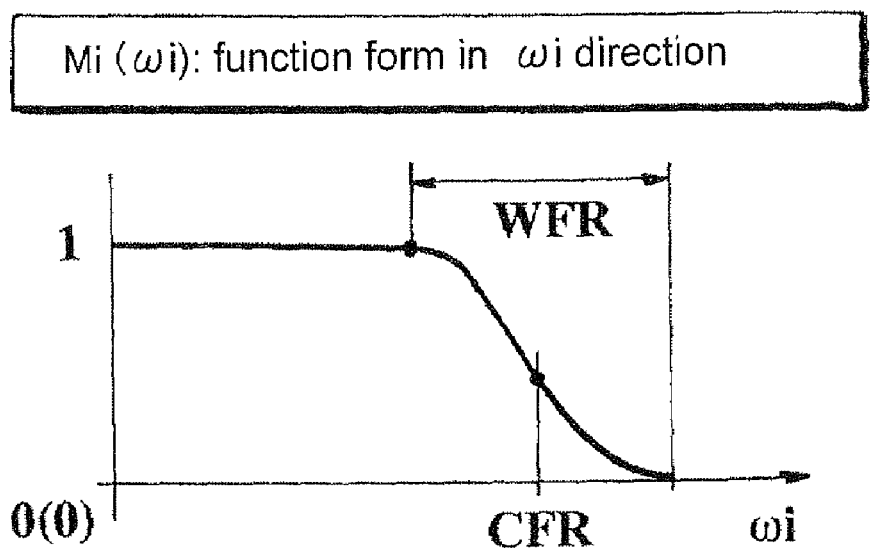
Figure 10B:
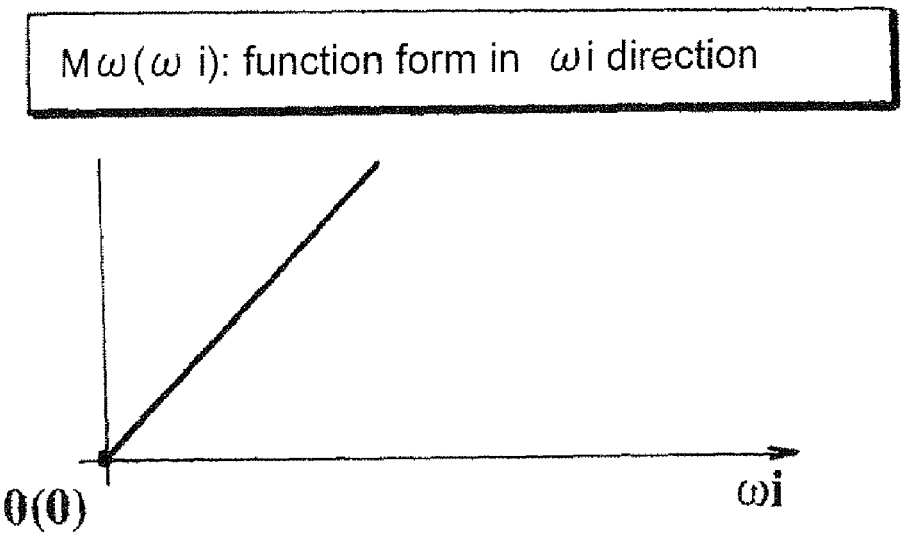

Mi (ωi) has a filter characteristic as shown in FIG. 10 (a), which is expressed by the following equations (7)-(9):

Feldkamp method $i < CFR - WFR/2$) (7)

$Mi(\omega i) = \{1 - \sin((\omega i - CFR)\cdot \pi/WFR)\}/2$ (where $CFR - WFR/2 < \omega i < CFR + WFR/2$) (8)

$Mi(\omega i) = 0$ (where $CFR + WFR/2 < \omega i$) (9)

However, the function has a sine wave form with high frequency components smoothly attenuating as shown in FIG. 10 (a). CFR is a cutoff frequency, and WFR is a total transition frequency width of filter strength (see FIG. 10 (a)). This Mi (ωi) deletes high frequency components from the one-dimensional Fourier space.

Mi (ωi) has a filter characteristic shown in FIG. 10 (b), which is expressed by the following equation (10):

$$M\omega(\omega i) = |\omega i| \quad (10)$$

FIGS. 10 (a) and (b) show only the characteristics in the plus direction along the horizontal axis. The characteristics in the minus direction along the horizontal axis are omitted since these are in linear symmetry with the characteristics in the plus direction about the vertical axis.

Reverting to FIG. 9, the one-dimensional inverse Fourier transform unit performs a one-dimensional inverse Fourier transform of the image in Fourier space SCF' (i, ω) |ω|-filtered by the |ω| filtering unit to put the image back to real space data and generate a convoluted projection image SC' (i, j).

Figure 11:
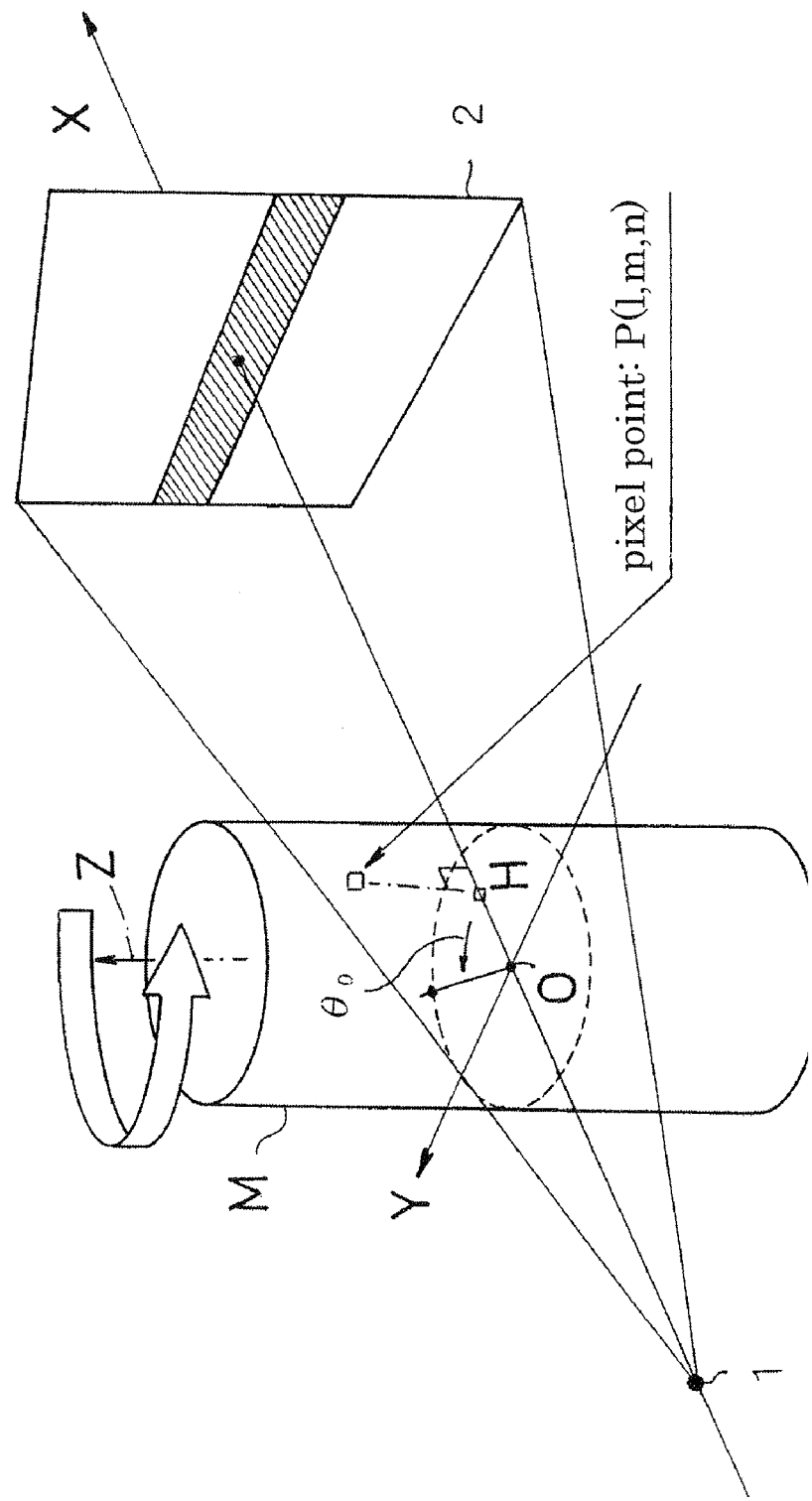

The second weighting unit 20C performs the second weighting process on the convoluted projection data SC' (i, j) for each scan position. Specifically, a weight function W (l, m, n) for a 3D pixel point: P (l, m, n) in a coordinate system applied to the patient (see FIG. 11) is derived from the following equation (11):

$$W(l,m,n) = RO^2/(RO+OH)^2 \quad (11)$$

where H is a position on the X-axis of a perpendicular extending from the pixel point P (l, m, n).

Figure 12:
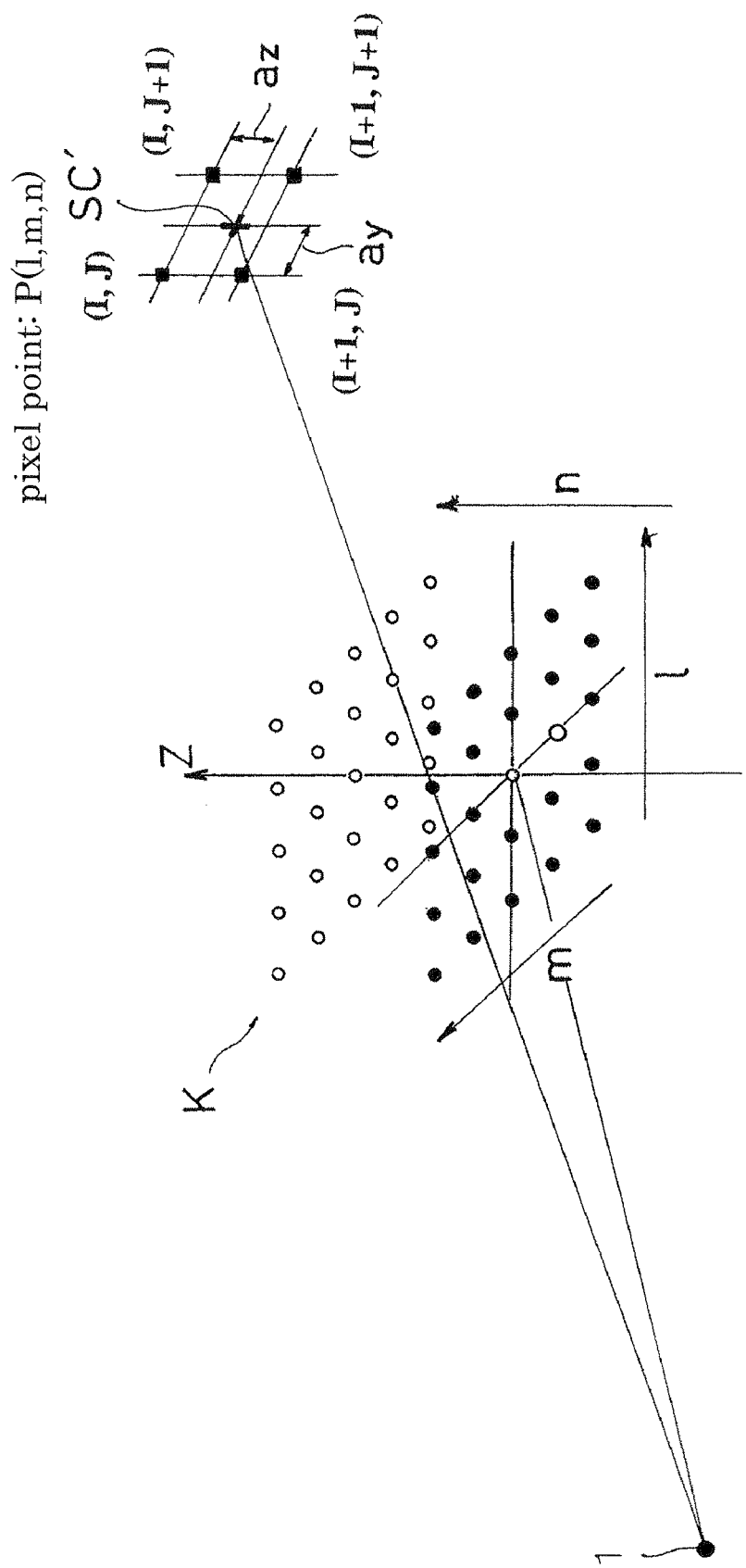

Then, as shown in FIG. 12, the second weighting unit 55 determines coordinates (I, J) of the projection image SC' (i, j) of the 3D pixel point: P (l, m, n), and weighting mantissa ($a_z$, $a_y$). The second weighting process is carried out as described above.

Next, the back projection unit 20D performs the predetermined back projection (BP) individually of the projection data after the second weighting process to generate a BP image (3D volume data). Specifically, an image reconstruction is performed to generate 3D volume data of the site of interest of patient M by projecting the group of projection data of the site of interest detected in the varied scan positions and having undergone the second weighting process, back to predetermined lattice points of a 3D lattice K virtually set to the site of interest as shown in FIG. 12. That is, the simple BP image noted hereinbefore is generated.

Specifically, a computation for linear interpolation and a back projection are carried out according to the following equation (12):

$$I_n(l,m,n) = I_{n-1}(l,m,n) + W(l,m,n) \times \{W_{11} \cdot SC'(I,J) + W_{12} \cdot SC'(I,J+1) + W_{21} \cdot SC'(I+1,J) + W_{22} \cdot SC'(I+1,J+1)\} \quad (12)$$

where $I_n$ (l, m, n) is an accumulation of back projection, and $I_{n-1}$ (l, m, n) is an accumulation of back projection made by preceding steps.

Pixel spacing of the projection image is standardized to 1, and weight functions in a multiplication weighting method as in the following equations (13)-(16) are used:

$$W_{11} = (1-a_z) \cdot (1-a_y) \quad (13)$$

$$W_{12} = (1-a_z) \cdot a_y \quad (14)$$

$$W_{21} = a_z \cdot (1-a_y) \quad (15)$$

$$W_{22} = a_z \cdot a_y \quad (16)$$

A similar back projection is performed on the remaining predetermined lattice points of 3D lattice K. Further, a similar back projection is performed for varied scan positions, i.e. over the range of +θmax (+110°) to −θmax (−110°) to generate a BP image (3D volume data).

The 3D image memory 21 stores the 3D volume data (3D image of blood vessels in this embodiment) generated by the back projection unit 20D. When the operating unit 23 is operated to select image information of any given slice, this image information is outputted to the display monitor 22.

The display monitor 22 has a function to display selected image information stored in the 3D image memory 21.

In the above embodiment, the revolution mechanism 3 sets two arcuate tracks on a circumferential track around the patient M to be opposed to each other across the patient M, moves the X-ray tube 1 on one of the arcuate tracks, and moves the FPD 2 on the other arcuate track in synchronism therewith to maintain a fixed distance from the X-ray tube R, to perform arcuate scanning. The convolution unit 20B performs a convolution process on projection data detected in varied scan positions. The back projection unit 20D performs an image reconstruction to generate 3D volume data of the site of interest by projecting the projection data having undergone the convolution process by the convolution unit 20B, back to predetermined lattice points of a 3D lattice K virtually set to the site of interest of the patient. This embodiment does not use the conventional method of generating 2D sectional image data by performing an addition computation of detection signals such as by superimposing on a single plane a plurality of projection images acquired through radiography from varied angles (projection images from varied scan positions). Instead, a convolution process is carried out on projection data detected in varied scan positions, and an image reconstruction is carried out to generate 3D volume data of the site of interest by projecting the projection data having undergone the convolution process, back to predetermined lattice points of the 3D lattice. It is thus possible to generate 3D volume data of the site of interest without executing a plurality of section radiographic steps, thereby quickly generating a 3D sectional image of the site of interest of the patient.

The 3D X-ray image acquired in the 3D reconstruction unit 20 is sent to and stored in the 3D image memory 21. The 3D X-ray image is read from the 3D image memory 21 as necessary, to be displayed on the screen of the display monitor 22, for example.

The display monitor 22 displays on its screen also a menu for performing operations required for X-ray photography and operation of the apparatus. When inputting commands and data required for X-ray photography or operation of the apparatus, the commands and data are inputted from the operating unit 23 using input devices such as a mouse and a keyboard. The main controller 24 is constructed mainly of a computer (CPU) and operation programs, and has an overall control function for always operating the entire apparatus appropriately, i.e. to transmit proper commands and data to required parts in a timely manner in response to various types of command inputted from the operating unit 23, or progress of X-ray photography.

Figure 13:
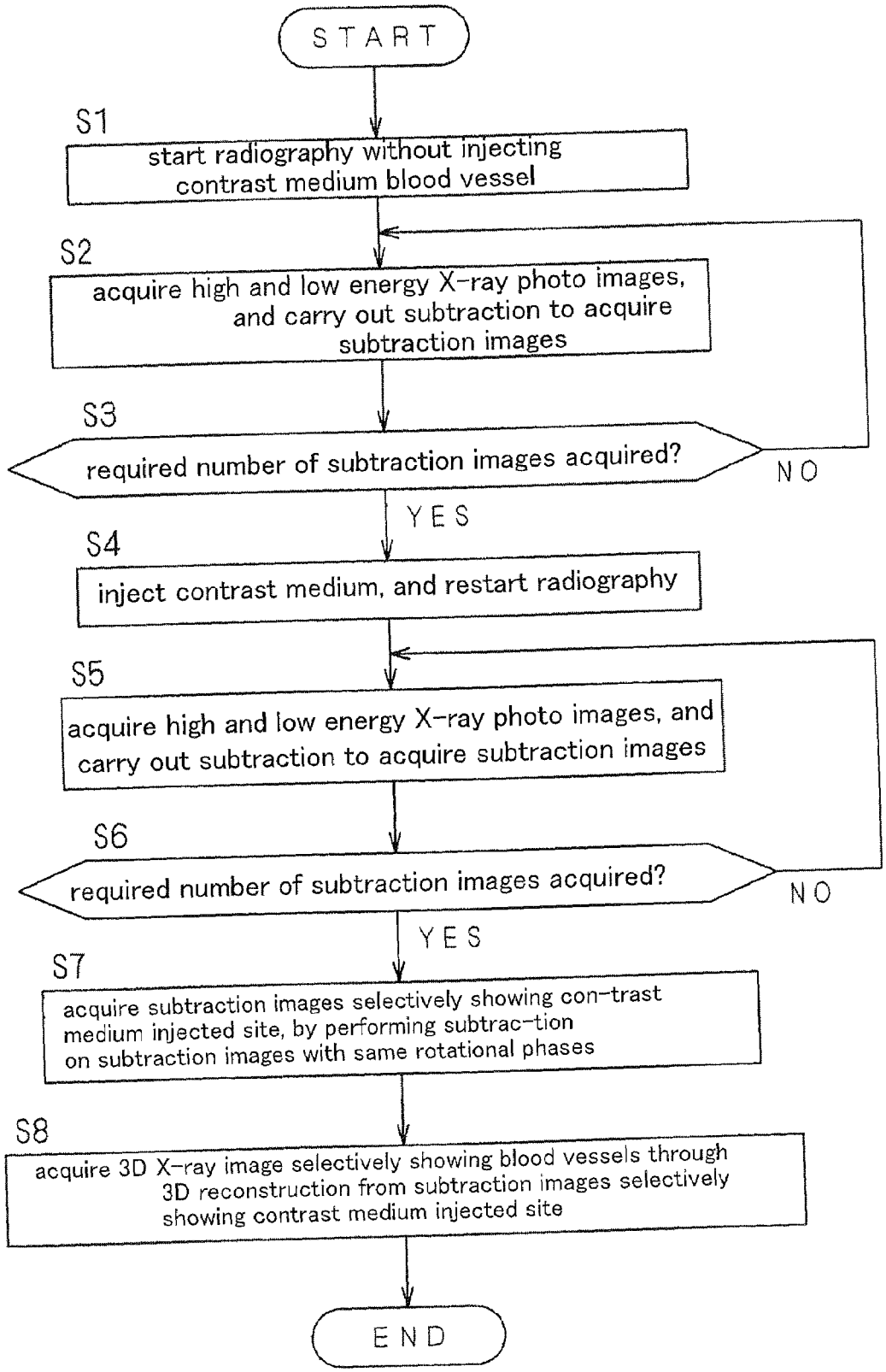

A radiographic process for obtaining a 3D X-ray image by the X-ray imaging apparatus having the above construction will be described with reference to the drawings. FIG. 13 is a flow chart showing the radiographic process for obtaining a 3D X-ray image by the X-ray imaging apparatus in this embodiment.

The following description is made on assumptions that the patient M is placed on the top board BD and set to a position for radiography, and that a 3D X-ray image to be finally obtained shows selectively blood vessels into which a contrast medium has been injected as a site of interest in the patient M. It is also assumed that factors a and b set are for the high energy X-ray photo images and low energy X-ray photo images, such that the energy subtraction unit 15 acquires, as subtraction images, images showing substantially only osseous parts such as the ribs or backbone.

[Step S1] The operator starts the apparatus to start X-ray radiography without injecting the contrast medium into the blood vessels of the patient M.

Figure 14:
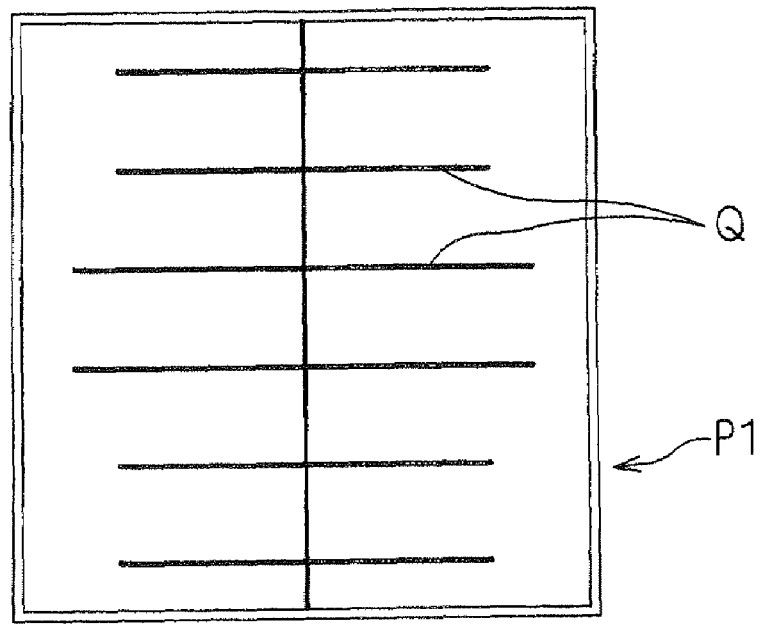

[Step S2] While the X-ray tube 1 and FPD 2 revolve about the patient M at a uniform speed, the X-ray beams of high energy and low energy are emitted alternately to acquire high energy X-ray photo images and low energy X-ray photo images. Then, the energy subtraction unit 15 carries out an image subtraction process on the high energy X-ray photo images and low energy X-ray photo images. As shown in FIG. 14, subtraction images P1 selectively showing only osseous parts Q of the patient M are acquired and stored in the first subtraction image memory 16.

[Step S3] If a required number of subtraction images P1 have not yet been acquired by the energy subtraction unit 15, the operation returns to step S2. If the required number of subtraction images P1 have already been acquired by the energy subtraction unit 15, the operation proceeds to following step S4.

[Step S4] The operator injects the contrast medium into the blood vessels of the patient M, and then restarts the apparatus to resume X-ray radiography.

Figure 15:
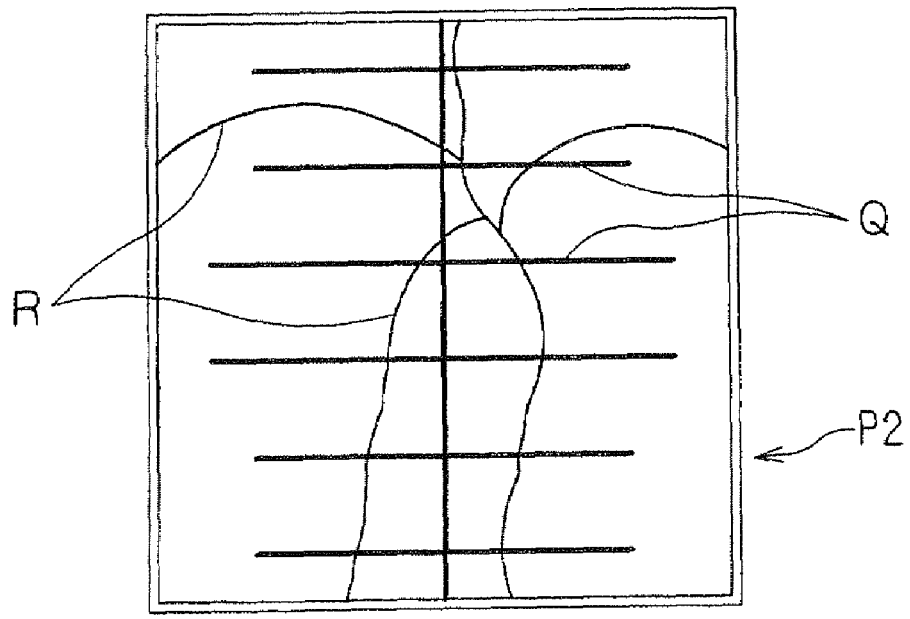

[Step S5] While the X-ray tube 1 and FPD 2 revolve about the patient M at a uniform speed, the X-ray beams of high energy and low energy are emitted alternately to acquire high energy X-ray photo images and low energy X-ray photo images. Then, the energy subtraction unit 15 carries out an image subtraction process on the high energy X-ray photo images and low energy X-ray photo images. As shown in FIG. 15, subtraction images P2 selectively showing osseous parts Q, and the blood vessels R into which the contrast medium has been injected, of the patient M are acquired and stored in the second subtraction image memory 17.

[Step S6] If a required number of subtraction images P2 have not yet been acquired by the energy subtraction unit 15, the operation returns to step S5. If the required number of subtraction images P2 have already been acquired by the energy subtraction unit 15, the operation proceeds to following step S7.

Figure 16:
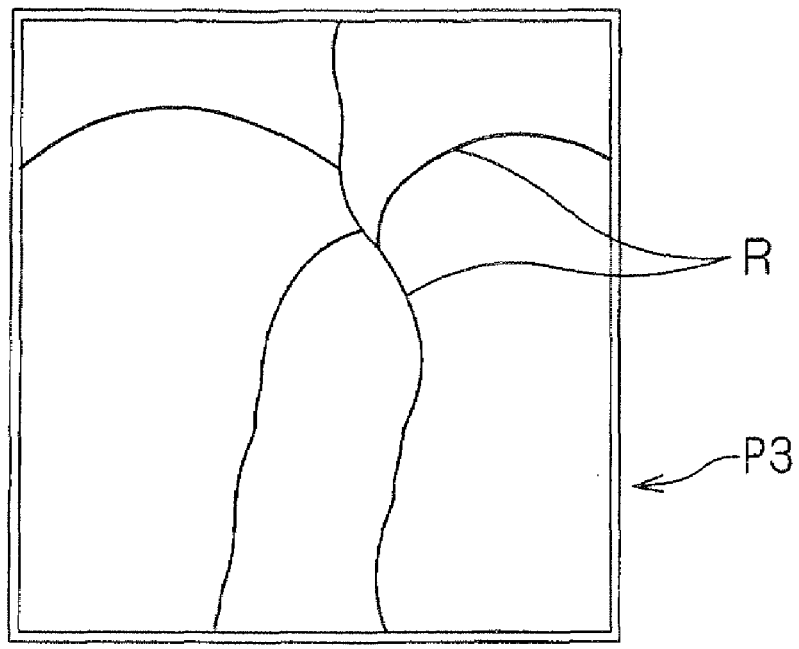

[Step S7] The contrast medium selecting subtraction unit 18 performs the image subtraction process on the subtraction images P1 and P2 stored in the first subtraction image memory 16 and second subtraction image memory 17 and having the same rotational phases. Consequently, as shown in FIG. 16, subtraction images P3 selectively showing the blood vessels R with the contrast medium injected, and eliminating the osseous parts, are successively acquired and stored in the contrast medium selective image memory 19.

Figure 17:
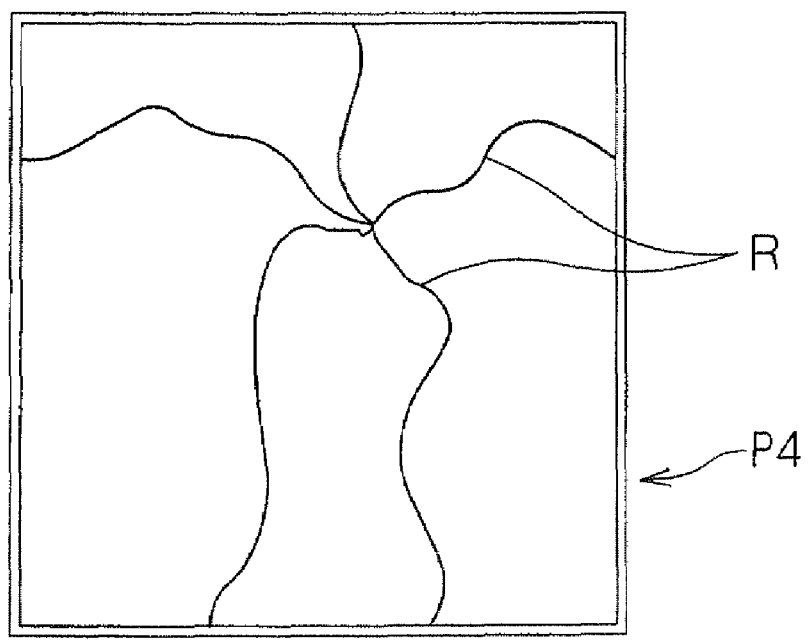
FIG. 17

[Step S8] The 3D reconstruction unit 20 performs the 3D reconstruction process to acquire, from the subtraction images stored in the contrast medium selective image memory 19, a 3D X-ray image P4 selectively showing only the blood vessels R into which the contrast medium has been injected, as shown in FIG. 17.

With the apparatus in this embodiment, as described above, the subtraction images obtained by the energy subtraction unit 15 serve as the basis for the 3D reconstruction process for acquiring a 3D X-ray image selectively showing the blood vessels into which the contrast medium has been injected as a site of interest in the patient M. In addition, the subtraction images obtained by the energy subtraction unit 15 select the blood vessels into which the contrast medium has been injected, and osseous parts, of the patient M as the site of interest, with the soft tissue forming a background around the site of interest eliminated, which are due to the weights set by the weight setter 14 to the high energy X-ray photo images and low energy X-ray photo images, and the image subtraction process of both the high and low energy X-ray photo images carried out by the energy subtraction unit 15 according to the weights set by the weight setter 14.

Therefore, even if body motion occurs with the soft tissue forming the background around the site of interest of the patient M while numerous subtraction images are acquired one after another by the energy subtraction unit 15, the soft tissue forming the background is eliminated from each subtraction image obtained by the energy subtraction unit 15. Consequently, the body motion in the soft tissue of the patient M is never reflected on the subtraction images, or on the 3D X-ray image acquired on the basis of the subtraction images.

Therefore, according to the X-ray imaging apparatus in this embodiment, artifacts due to a body motion of the patient M is prevented from appearing in the 3D X-ray image selectively showing the blood vessels into which the contrast medium has been injected as a site of interest in the patient M.

In addition, in the apparatus in this embodiment, the X-ray tube 1 and FPD 2 are revolved by the revolution mechanism 3 through 180 degrees or more about the object under examination. The subtraction images serving as the basis for the 3D reconstruction process for acquiring a 3D X-ray image arc obtained over a large range of 180 degrees or more. This allows the 3D reconstruction process for acquiring a 3D X-ray image to be carried out with high precision.

Embodiment 2

Figure 18:
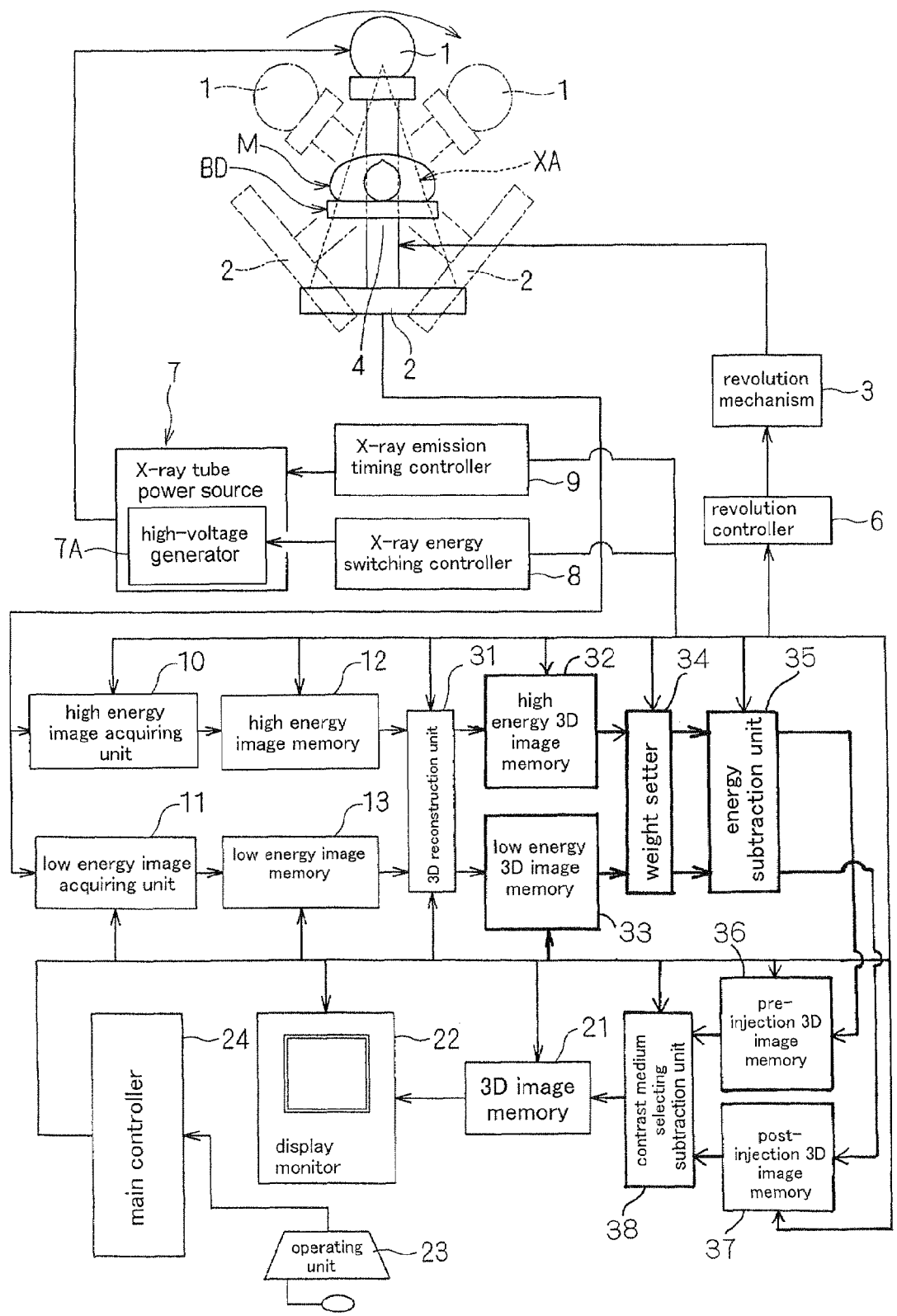

FIG. 18 is a block diagram showing an overall construction of an X-ray imaging apparatus in a second embodiment.

The elements affixed with the same reference signs as in FIG. 1 have the same constructions as in the X-ray imaging apparatus in the first embodiment, and will not be described here.

With the X-ray imaging apparatus in the first embodiment, subtraction images are obtained through a weighted energy subtraction process of the high energy X-ray photo images and low energy X-ray photo images acquired adjacent each other in time, and a 3D image is obtained through a 3D reconstruction process carried out on the basis of these subtraction images. Since the X-ray tube 1 and FPD 2 acquire the high energy X-ray photo images and low energy X-ray photo images while revolving around the patient M, slight displacements occur between the high energy X-ray photo images and low energy X-ray photo images. As a result, the subtraction images subjected to the 3D reconstruction process include blurs due to the displacements, which will appear as artifacts in time of the 3D reconstruction process.

On the other hand, the X-ray imaging apparatus in the second embodiment carries out 3D reconstruction processes separately for the high energy X-ray photo images and low energy X-ray photo images acquired adjacent each other in time, to acquire a 3D image by high energy X-ray radiography and a 3D image by low energy X-ray radiography. A 3D subtraction image is obtained through a weighted energy subtraction process carried out for both the high and low 3D images. In this way, each of the high energy X-ray photo images and low energy X-ray photo images used as the basis for the 3D reconstruction process is free from a displacement as occurring in the first embodiment, thereby reducing artifacts in time of the 3D reconstruction process.

In the first embodiment, the weighted energy subtraction process is carried out before the 3D reconstruction process. When a 3D image finally obtained is observed and the weighting factors are changed, a 3D image must be obtained by carrying the 3D reconstruction process imposing a heavy processing burden again. Therefore, the weighting factors cannot be changed at will. In the second embodiment, on the other hand, 3D reconstruction processes are carried out separately beforehand for the high energy X-ray photo images and low energy X-ray photo images, and a weighted subtraction process is carried out afterward. Thus, even when the weighting factors are changed, it is unnecessary to repeat the 3D reconstruction process imposing a heavy processing burden. Therefore, the weighting factors can be changed at will, and optimal weighting factors can be set. This enables a high-quality energy subtraction image to be obtained easily.

A characteristic construction of the X-ray imaging apparatus in the second embodiment will be described hereinafter with reference to FIG. 18.

This X-ray imaging apparatus has a 3D reconstruction unit 31 for acquiring a 3D image of high energy X-ray radiography by carrying out a 3D reconstruction process on the basis of numerous high energy X-ray photo images around the object under examination accumulated in the high energy image memory 12, and acquiring a 3D image of low energy X-ray radiography by carrying out a 3D reconstruction process on the basis of numerous low energy X-ray photo images around the object under examination accumulated in the low energy image memory 13. The 3D image of high energy X-ray radiography is stored in a high energy 3D image memory 32, and the low energy 3D image of low energy X-ray radiography in a low energy 3D image memory 33.

A weight setter 34 sets suitable weighting factors to select a site of interest in the patient with respect to the 3D image of high energy X-ray radiography and 3D image of low energy X-ray radiography. Further, an energy subtraction unit 35 disposed downstream carries out a subtraction process on the 3D image of high energy X-ray radiography and the 3D image of low energy X-ray radiography to obtain a 3D subtraction image including the site of interest of the patient.

The 3D subtraction image before injection of the contrast medium is stored in a pre-injection 3D image memory 36, and the 3D subtraction image after injection of the contrast medium is stored in a post-injection 3D image memory 37. A contrast medium selecting subtraction unit 38 carries out a subtraction process on the 3D subtraction image before injection of the contrast medium and the 3D subtraction image after injection of the contrast medium, to obtain a 3D subtraction image of the contrast medium injected site (3D image of blood vessels). This 3D subtraction image is displayed on the display monitor 22 through the 3D image memory 21.

Figure 19:
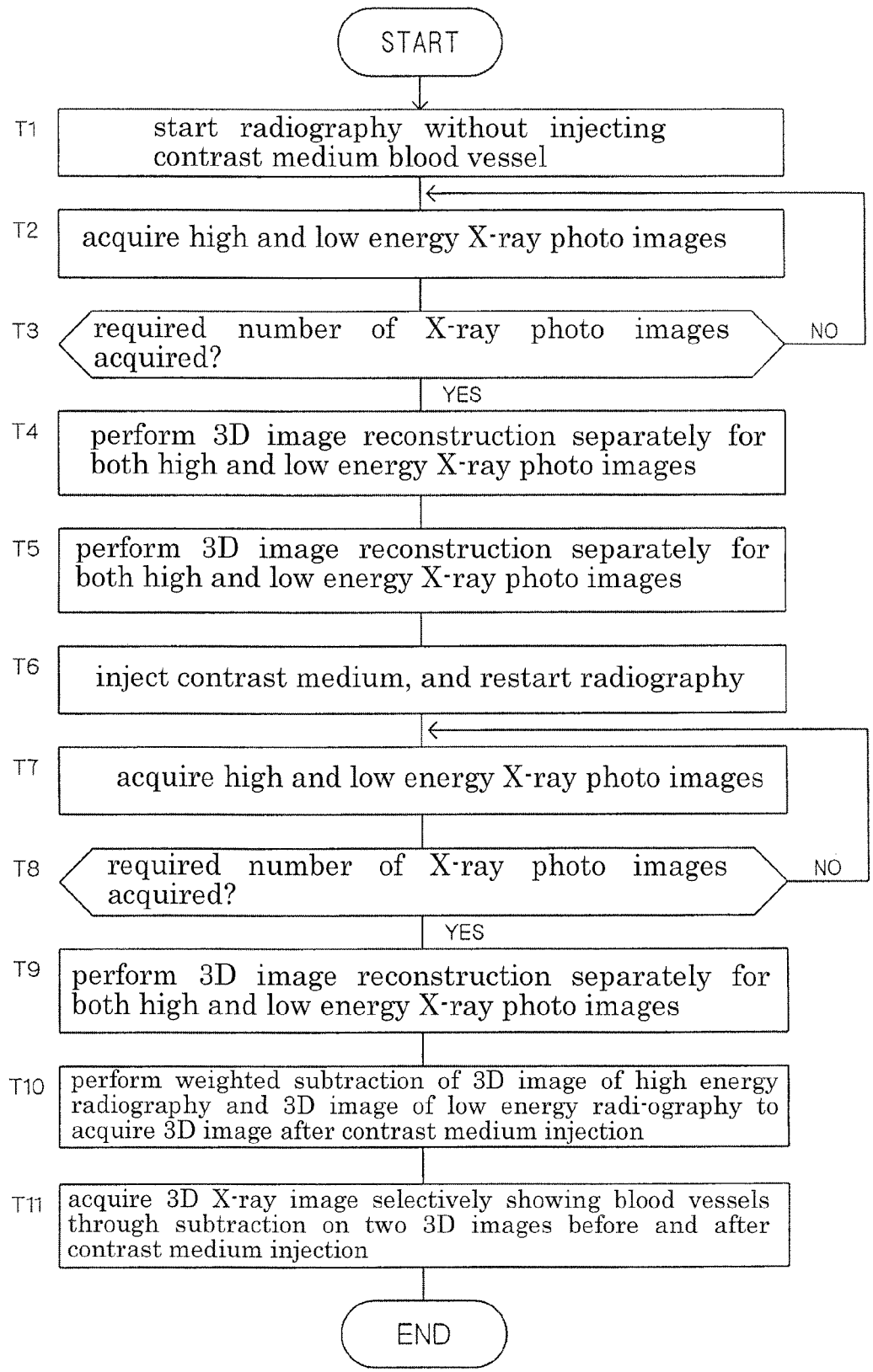

A radiographic process for obtaining a 3D X-ray image by the X-ray imaging apparatus having the above construction will be described with reference to the drawings. FIG. 19 is a flow chart showing the radiographic process for obtaining a 3D X-ray image by the X-ray imaging apparatus in the second embodiment.

[Step T1] The operator starts the apparatus to start X-ray radiography without injecting the contrast medium into the blood vessels of the patient M.

[Step T2] While the X-ray tube 1 and FPD 2 revolve about the patient M at a uniform speed, the X-ray beams of high energy and low energy are emitted alternately to acquire high energy X-ray photo images and low energy X-ray photo images.

[Steps T3, T4] If a required number of high and low energy X-ray photo images have been acquired, a 3D image reconstruction is carried out separately for both high and low energy X-ray photo images to obtain a 3D image of high energy X-ray radiography and a 3D image of low energy X-ray radiography.

[Step T5] A weighted subtraction is carried out for the 3D image of high energy radiography and 3D image of low energy radiography to acquire a 3D image before contrast medium injection.

[Step T6] The operator injects the contrast medium into the blood vessels of the patient M, and then restarts the apparatus to resume X-ray radiography.

[Steps T7-T10] Processes similar to steps T2-T5 above are carried out to acquire a 3D image after contrast medium injection.

[Step T11] A 3D X-ray image selectively showing the blood vessels through a subtraction carried out on the 3D image before contrast medium injection and the 3D image after contrast medium injection.

With the apparatus in the second embodiment, as described above, 3D reconstruction processes are first carried out on the basis of high energy X-ray photo images and low energy X-ray photo images, to acquire a 3D image of high energy X-ray radiography and a 3D image of low energy X-ray radiography. A weighted energy subtraction process is carried out on these two 3D images. Thus, there is little possibility of artifacts due to displacements occurring in time of the 3D reconstruction process. Further, optimal weighting factors can easily be set, to realize a high-quality 3D subtraction image.

This invention is not limited to the foregoing embodiments, but may be modified as follows:

(1) The apparatus in the embodiments are constructed for carrying out angiography. The second subtraction image memory 17, contrast medium selecting subtraction unit 18 and contrast medium selective image memory 19 may be omitted, resulting in a construction for using subtraction images obtained by the energy subtraction unit 15 and stored in the first subtraction image memory 16 to acquire a 3D X-ray image selectively showing, for example, osseous parts as a site of interest in the patient M, or selectively showing, conversely, for example, soft tissue as a site of interest in the patient M.

(2) In the apparatus in the embodiment, the contrast medium selecting subtraction unit 18 carries out an image subtraction process superimposing the subtraction images stored in the first subtraction image memory 16 and second subtraction image memory 17, and thereafter a 3D reconstruction process is carried out by the 3D reconstruction unit 20. A modified example of the apparatus may be constructed such that a 3D reconstruction process is carried out using the subtraction images stored in the first subtraction image memory 16 to obtain a 3D X-ray image, a 3D reconstruction process is carried out using the subtraction images stored in the second subtraction image memory 17 to obtain a 3D X-ray image, and then an image subtraction process is carried out for the 3D X-ray images obtained. The modified apparatus can also acquire the same 3D X-ray image as acquired with the apparatus in the embodiment. However, the apparatus in the embodiment has an advantage of requiring the 3D reconstruction process having a heavy processing load to be carried out only once.

(3) In the apparatus in the embodiment, the two-dimensional X-ray detecting device is an FPD. The two-dimensional X-ray detecting device is not limited to an FPD, but may be an image intensifier, for example.

Figure 20:
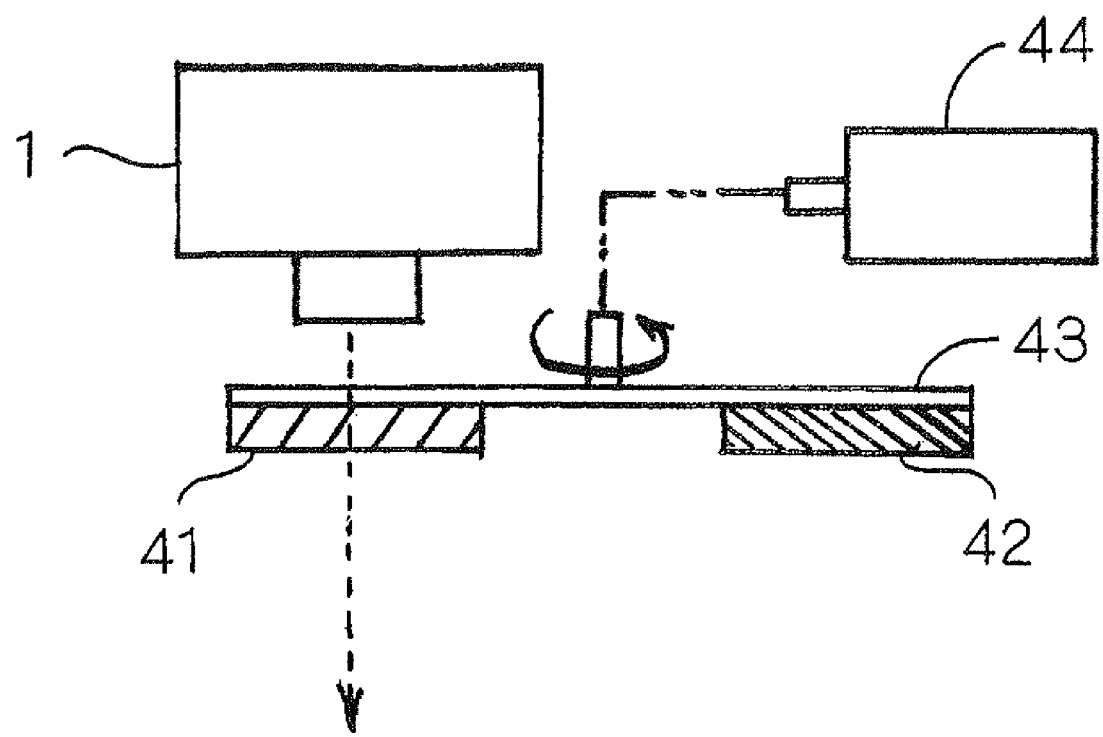

(4) In the foregoing embodiments, the X-ray beam of high energy and the X-ray beam of low energy are emitted alternately by switching the voltage applied to the X-ray tube 1 between high voltage and low voltage. However, the X-ray energy switching control device in this invention is not limited to such an example. The X-ray tube 1 may emit an X-ray beam of fixed energy. This X-ray beam may be transmitted through a low energy absorption member to produce a high energy X-ray beam. Further, this X-ray beam may be transmitted through a high energy absorption member to produce a low energy X-ray beam. In the example shown in FIG. 20, an X-ray absorbing filter with a low energy absorption member 41 and a high energy absorption member 42 attached to a rotatable disk 43 is disposed adjacent an X-ray beam exit aperture of X-ray tube 1. By rotating this disk 43 with a motor 44, an X-ray beam of high energy and an X-ray beam of low energy are emitted alternately.

The invention claimed is:

1. An X-ray imaging apparatus characterized by comprising (A) an X-ray beam emitting device for emitting X-ray beams to an object under examination to be radiographed; (B) a two-dimensional X-ray detecting device for detecting transmitted X-ray images of the object under examination produced by emission of the X-ray beams to the object under examination, and outputting X-ray detection signals in real time; (C) a revolution device for revolving the X-ray beam emitting device and the two-dimensional X-ray detecting device about the object under examination as opposed to each other with the object under examination in between; (D) an X-ray energy switching control device for performing X-ray energy switching control to switch the X-ray beams emitted from the X-ray beam emitting device alternately to high energy X-ray beams of high energy and to low energy X-ray beams of low energy; (E) a high energy image acquiring device for acquiring high energy X-ray photo images based on X-ray detection signals outputted from the two-dimensional X-ray detecting device as a result of emission of the high energy X-ray beams; (F) a low energy image acquiring device for acquiring low energy X-ray photo images based on X-ray detection signals outputted from the two-dimensional X-ray detecting device as a result of emission of the low energy X-ray beams; (J) a 3D reconstruction device for carrying out a 3D reconstruction process based on the high energy X-ray photo images to acquire a 3D X-ray image of high energy X-ray radiography, and a 3D reconstruction process based on the low energy X-ray photo images to acquire a 3D X-ray image of low energy X-ray radiography; (K) a weight setting device for setting weights suitable for selecting a site of interest in the object under examination with respect to the 3D X-ray image of high energy X-ray radiography and 3D X-ray image of low energy X-ray radiography; and (L) an energy difference using subtraction device for acquiring a 3D subtraction image through an image subtraction process carried out, according to the weights set by the weight setting device, on the 3D X-ray image of high energy X-ray radiography and 3D X-ray image of low energy X-ray radiography.

2. An X-ray imaging apparatus as defined in claim 1, comprising a contrast medium using subtraction device for acquiring a subtraction image selecting a contrast medium injected site through an image subtraction process carried out on images of the object under examination before a contrast medium is injected and on images of the object under examination after the contrast medium is injected.

3. An X-ray imaging apparatus as defined in claim 2, wherein the contrast medium using subtraction device carries out the image subtraction process on the subtraction images, acquired by the energy subtraction device, of the object under examination before and after the contrast medium is injected, respectively, and the 3D reconstruction device carries out the 3D reconstruction process using the subtraction images acquired by the contrast medium using subtraction device.

4. An X-ray imaging apparatus as defined in claim 1, wherein the X-ray beam emitting device and the two-dimensional X-ray detecting device are attached separately to one end and the other end of a C-shaped arm to be opposed to each other.

5. An X-ray imaging apparatus as defined in claim 4, wherein a revolution device revolves the X-ray beam emitting device and the two-dimensional X-ray detecting device through at least 180 degrees about the object under examination.

6. An X-ray imaging apparatus as defined in claim 5, wherein the revolution device drives the X-ray beam emitting device and the two-dimensional X-ray detecting device for accelerated revolution, uniform speed revolution and decelerated revolution in order, the X-ray beams being emitted while the X-ray beam emitting device and the two-dimensional X-ray detecting device are driven for the uniform speed revolution.

7. An X-ray imaging apparatus as defined in claim 1, wherein the X-ray energy switching control device applies a high voltage to the X-ray beam emitting device to emit the high energy X-ray beams of high energy, and applies a low voltage to the X-ray beam emitting device to emit the low energy X-ray beams of low energy.

8. An X-ray imaging apparatus as defined in claim 1, wherein the X-ray energy switching control device causes the X-ray beams emitted from the X-ray beam emitting device to pass through a low energy absorbing member, thereby to emit the high energy X-ray beams of high energy, and causes the X-ray beams emitted from the X-ray beam emitting device to pass through a high energy absorbing member, thereby to emit the low energy X-ray beams of low energy.

* * * * *